(12) United States Patent
Cyr et al.

(10) Patent No.: US 9,205,122 B2
(45) Date of Patent: Dec. 8, 2015

(54) HERBAL COMPOSITION COMPRISING GINGER AND GOLDENROD FOR THE TREATMENT OF COLD AND FLU

(75) Inventors: Benoit Cyr, Saint-Augustin-de-Desmaures (CA); Johane Guay, Saint-Augustin-de-Desmaures (CA); Brigitte Page, Quebec (CA); Nathalie Gendron, Saint-Basile-de-Portneuf (CA)

(73) Assignee: MARESINS PHARMA, INC., Quebec (CA)

( * ) Notice: Subject to any disclaimer, the term of this patent is extended or adjusted under 35 U.S.C. 154(b) by 346 days.

(21) Appl. No.: 13/503,097

(22) PCT Filed: Oct. 22, 2010

(86) PCT No.: PCT/CA2010/001657
§ 371 (c)(1),
(2), (4) Date: Apr. 20, 2012

(87) PCT Pub. No.: WO2011/047473
PCT Pub. Date: Apr. 28, 2011

(65) Prior Publication Data
US 2012/0201911 A1    Aug. 9, 2012

Related U.S. Application Data

(60) Provisional application No. 61/254,031, filed on Oct. 22, 2009, provisional application No. 61/308,052, filed on Feb. 25, 2010.

(51) Int. Cl.
*A61K 36/906* (2006.01)
*A61K 36/28* (2006.01)
*A61K 9/48* (2006.01)
*A61K 36/9068* (2006.01)
*A61K 9/00* (2006.01)

(52) U.S. Cl.
CPC .............. *A61K 36/28* (2013.01); *A61K 9/4866* (2013.01); *A61K 36/9068* (2013.01); *A61K 9/0095* (2013.01)

(58) Field of Classification Search
None
See application file for complete search history.

(56) References Cited

U.S. PATENT DOCUMENTS

| | | | |
|---|---|---|---|
| 7,166,435 | B2 | 1/2007 | Rosenbloom |
| 7,205,010 | B2 | 4/2007 | Sha |
| 2003/0099730 | A1* | 5/2003 | Rosenbloom ............... 424/755 |
| 2004/0175439 | A1 | 9/2004 | Cyr |
| 2007/0248693 | A1 | 10/2007 | Mazzio |
| 2008/0102140 | A1 | 5/2008 | Lou |
| 2008/0254143 | A1* | 10/2008 | Heuer et al. ................. 424/641 |
| 2009/0004302 | A1 | 1/2009 | Cyr |
| 2009/0068291 | A1 | 3/2009 | Cyr |

FOREIGN PATENT DOCUMENTS

| | | |
|---|---|---|
| CA | 1192108 | 8/1985 |
| CN | 1451434 A | 10/2003 |
| CN | 1931208 A | 3/2007 |
| CN | 101130028 | 2/2008 |
| CN | 101365466 A | 2/2009 |
| WO | 02069992 A1 | 9/2002 |
| WO | 2004012655 A2 | 2/2004 |
| WO | 2004019961 A1 | 3/2004 |
| WO | 2006037513 A1 | 4/2006 |
| WO | 2007056811 A1 | 5/2007 |

OTHER PUBLICATIONS

UMM. Internet Archive date: Apr. 27, 2007 [Retrieved from the Internet on: Apr. 22, 2013]. Retrieved from: <URL: http://web.archive.org/web/20070427120233/http://www.umm.edu/altmed/articles/goldenrod-000251.htm>.*
Altman, L.K., This Season's Flu Virus is Resistant to 2 Standard Drugs, New York Times (The New York Times Company), Jan. 15, 2006.
Blumenthal, M. et al., The complete German Commission E monographs. Therapeutic guide to herbal medicines. American Botanical Council., 1998, pp. 135-140.
Bridges, CB, et al., Effectiveness and cost-benefit of influenza vaccination of healthy working adults: a randomized controlled trial, JAMA, 2000;284:1655-63.
Cottey R., et al., Inflenza virus, Current protocol in Immunology, May 2001; Chapter 19 :Unit19.11.
Gubareva, LV, Molecular mechanisms of influenza virus resistance to neuraminidase inhibitors, Virus Research, (2004), 103: 199-203.
Hayden, FG, et al., Plaque inhibition assay for drug susceptibility testing on influenza viruses, Antimicrobial Agents and Chemotherapy, (1980), 17(5) :865-870.
Hawkins, E.B., et al., Goldenrod, A.D.A.M.S. Inc., (Jan. 17, 2007), metagenics.com/ADAM/33/000251.html.
Hendrickson, R. Ed., Remington: The Science and Practice of Pharmacy, 21st ed., 2005, Lippincott Williams & Wilkins: Baltimore MD.
Herrera, GA, et al., Influenza vaccine effectiveness among 50-64-year-old persons during a season of poor antigenic match between vaccine and circulating influenza virus strains: Colorado, United States, 2003-2004, Vaccine, 2007, 25(1):154-160.
Hoffman, D.L., Goldenrod, Herbal Materia, Medica, Health World Online, 2009.

(Continued)

*Primary Examiner* — Terry A McKelvey
*Assistant Examiner* — Catheryne Chen
(74) *Attorney, Agent, or Firm* — Goudreau Gage Dubuc; Julie Gauvreau

(57) ABSTRACT

Described herein is a composition comprising a combination of ginger and goldenrod for the prevention and/or treatment of cold and/or flu infection. Also described is a method of treating or preventing a cold and/or flu infection in a subject in need thereof comprising administering to the subject an effective amount of a composition comprising a combination of ginger and goldenrod.

44 Claims, 9 Drawing Sheets

(56) References Cited

OTHER PUBLICATIONS

Imanishi M., et al., Macrophage-mediated inhibitory effect of Zingiber Officinale Rosc, a traditional oriental herbal medicine, on the growth of influenza, Am J. Chin. Med., (2006), 34(1):157-169.
Klenk et al., Avian Influenza: Molecular Mechanisms of Pathogenesis and Host Range, Animal Viruses: Molecular Biology, 2008, Caister Academic Press, ISBN 978-1-904455-22-6-ABSTRACT.
Nema, S., et al., Excipients and their use in injectable products, PDA J. of Pharm. Science and Technol., 1997, 51(4), 166-171.
Noah, J.W., et al., Antiviral Res., A cell-based luminescence assay is effective for high-throughput screening of potential inluenza antivirals, Jan. 2007, 73(1):50-9.
Park, K.J., et al., Antiviral activity of aqueous extracts from korean medicinal plants against influenza virus Type A, J. Microbiol. Biotechnol., 2005, 15(5): 924-929.
Roomi, M.W., et al., Inhibition of cellular invasive parameters in influenza A virus-infected MDCK and Vero cells by a nutrient mixture, BioFactors, 2008, 33(1): 61-75.
Fiala, M., Plaque Formation by 55 Rhinovirus Serotypes, Appl Environ Microbiol., 1968, 16(10): 1445-1450.
Roxas, M., et al., Colds and Influenza: A review of diagnosis and conventional, botanical, and nutritional considerations, Alternative Medicine Review, 2007, 12-1:25-48.
Smith, N.M., et al., Prevention and Control of Influenza: Recommendations of the Advisory Committee on Immunization Practices (ACIP), Morbidity and Mortality Weekly Report, (Jul. 28, 2006), Centers for Disease Control and Prevention, 55(RR10): 1-42, http://www.cdc.gov/mmwr/preview/munwrhtml/rr5510a1.htm.
British Herbal Pharmacopae, Virgaurea, British Herbal Medicine Association, 1983, Megaron Press Ltd, Bournmouth, United Kingdom, p. 234-235.
Chinese medicine news, Ginger does ward-off flu: study, (Apr. 13, 2007) Chinesemedicinenews.com/2007/04/13/Ginger-does-ward-off-flu.
Gardens Ablaze, Medicinal Uses of Goldenrod, 2009, www.gardensablaze.com/HerbGoldenrodMed.htm.
Herbs of Mexico, Golden Rod Herb C/S/ Valla De Oro, 2009, herbsofmexico.com/store/index.
Tea benefits, Golden rod tea benefits, 2009, www.teabenefits.com/herbal-tea-benefits/goldenrod-tea-benefits.html.
Biopharmacopae Inc., The efficacy and safety of a natural patent pending combination of ginger and goldenrod on the management of cold symptoms in community-dwelling adults: A randomized, double blind controlled trial, Poster at 4th International Conference on Drug Discovery and Therapy, (Feb. 12, 2012), Dubai, UAE.
International Preliminary Report on Patentability in PCT/CA2010/001657 mailed May, 3, 2012.
Written Opinion and International Search Report in PCT/CA2010/001657 mailed Jan. 13, 2011.
Office Action issued Jul. 8, 2014 in Australian corresponding Application No. 2010310406.
Extended European search report issued Apr. 23, 2013 in European corresponding Application No. 10824348.6.
Office Action issued Jun. 13, 2014 in Chinese corresponding Application No. 201080046594.X.
Office Action issued Jan. 28, 2013 in Canadian corresponding Application No. 2,778,414.
Office Action issued Aug. 9, 2012 in Canadian corresponding Application No. 2,778,414.
Lou S., "Application of common goldenrod herb in preparing medicine for preventing and treating H5N1 bird flu and influenza"., Thomson (2007). Abstract of CN1931208A. XP-002557427.
Lou S.,"Chinese medicine for preventing and treating SARS virus", Thomson (2003). Abstract of CN1451434. XP002695351.
Chou et al., "Quantitative Analysis of Dose-Effect Relationships: The Combined Effects of Multiple Drugs or Enzyme Inhibitors", , pp. 27-55. XP23796270A.
Weed, Susun, "Glorious Goldenrod", XP55059356A, (2006).www.sunweed.com.
Office Action issued Jul. 13, 2015 in Australian corresponding Application No. 2010310406.

\* cited by examiner

HERBAL COMPOSITION COMPRISING GINGER AND GOLDENROD FOR THE TREATMENT OF COLD AND FLU

CROSS REFERENCE TO RELATED APPLICATIONS

This application is a national entry application of PCT application no PCT/CA2010/001657 filed on Oct. 22, 2010 and published in English under PCT Article 21(2), which itself claims benefit of U.S. provisional application Ser. No. 61/254,031, filed on 22 Oct. 2009 and No. 61/308,052, filed on 25 Feb. 2010. All documents above are incorporated herein in their entirety by reference.

FIELD OF THE INVENTION

The present invention relates to the prevention and/or treatment of cold and/or flu infections. More specifically, the present invention is concerned with a combination of ginger and goldenrod for use in pharmaceutical and/or nutritional compositions and methods for preventing and/or treating cold and/or flu infections or their symptoms.

BACKGROUND OF THE INVENTION

Flu

Flu is a contagious illness caused by the influenza virus. Common flu is characterized by an acute infection associated with respiratory problems, intense muscle pain (myalgia), headaches, chills, nasal obstruction, fever, cough, sneezing and sore throat. The majority of the population will generally recover from flu without any complication. Older people, young children and people with deficient immune systems, may have serious complications or may even die from the flu.

Current literature describes human common influenza as a serious disease causing each year an estimated 36,000 deaths in the United States only (Roxas, 2007). Yearly common influenza (flu) epidemics result in lost workdays and schooldays as well as a significant number of hospitalization days and even deaths among the elderly, seniors being particularly vulnerable to respiratory infections.

Flu is caused by the influenza virus strain A or B, but strain A is usually the one responsible for a pandemic flu (Klenk, 2008). There are several strain A subtypes, labeled according to an H number (for the type of hemagglutinin) and an N number (for the type of neuraminidase). There are 16 different H antigens (H1 to H16) and nine different N antigens (N1 to N9). Influenza A (H1N1) virus is a subtype of influenza A virus and the most common cause of influenza (flu) in humans. Some strains of H1N1 are endemic in humans and cause a fraction of all influenza-like illness and a fraction of all seasonal influenza. The Pandemic H1N1/09 virus is a swine origin Influenza A virus subtype H1N1 virus strain responsible for the 2009 flu pandemic. Flu treatment is possible with drugs such as Oseltamivir (Tamiflu®, Roche) or Zanamivir; which are both inhibitors of neuraminidase, an important enzyme on the surface of the influenza virus (Gubareva L V, 2004). Viruses from the influenza family are known to present a high mutation rate and modifications to their genome may occur every single year, resulting in drug resistance. For example, cases have been observed where the influenza virus strain presented a high resistance to Tamiflu™ treatment (US Centers for Disease Control (CDC)).

New influenza strains infecting humans therefore appear from time to time. These strains frequently originate from other species and have adapted to human through mutations. The swine influenza A H1N1 flu virus, also named Swine Flu, has been reported around the world and was declared a pandemic influenza virus. Swine flu H1N1 originally only affected pigs but started infecting humans in North America in 2009. Humans having little to no natural immunity to this virus, it can lead to a serious and widespread illness.

Vaccines can prevent flu in 70 to 90% of the cases observed in healthy adults (Bridges C B, 2000; Herrera G A, 2007). However, the flu vaccine has to be redesigned each year because the previous years vaccines are likely to be ineffective against the newly mutated strains. The yearly vaccine is therefore designed before the season begins based on that from the previous year. Since scientists usually cannot predict with accuracy which strain will be dominant, the vaccine may not fully correspond to the new strain. In addition, the flu vaccine is specifically designed against influenza virus strains A and B and does not therefore protect against cold viruses such as rhinovirus and corona types.

Flu symptoms can be alleviated with either the previously mentioned treatment or with, for example, 1) over-the-counter analgesics to relieve pain and reduce fever; 2) cough suppressants for dry cough with no mucus; 3) expectorants to help clear mucus so it can be coughed up; and/or 4) decongestants to reduce nasal congestion.

Cold

The common cold is a very frequent acute illness in industrialized societies and the leading cause of visits to the physicians in the United States (Roxas, 2007). Though it is usually benign, it is a leading cause of absence from work, also causing an significant economic burden including loss of productivity and treatment costs. The common cold is caused by a variety of viruses, most of the time of the rhinovirus and corona types. There is currently no cure for common cold, so that current therapy targets symptoms relief. Prevention strategies for the common cold include avoiding infected people and frequent hand washing during cold season.

Conventional therapies have a limited efficacy. Certain drugs are costly and have side effects. Dietary supplements (e.g., *Echinacea*, ginseng, etc.) are often believed to be effective, but they lack formal studies using modern culture methods.

There remains a need for alternative compositions for the prevention and/or treatment of cold and/or flu infections.

The present description refers to a number of documents, the content of which is herein incorporated by reference in their entirety.

SUMMARY OF THE INVENTION

Applicants have identified and characterized new properties for a combination of two plants or parts thereof (e.g., their extracts). The combination of the present invention possesses activities which include antiviral in vitro and in vivo capabilities.

The two main active components of the combination of the present invention are: 1) ginger; and 2) goldenrod. As used herein, and unless the context in which they occur implicitly or explicitly suggest another meaning for these terms, the terms "ginger" and "goldenrod" refer the whole plants, parts thereof or extracts thereof. These plants and their extracts are recognized as safe substances for humans (German Commission E, Blumenthal M, 1998). Applicants have demonstrated that these plants alone or in combination are effective in preventing and/or treating cold and/or flu infections. In addition, Applicants discovered that goldenrod and ginger act together and demonstrate a strong (more than additive) antiviral activity, including the inhibition of the influenza virus (Strain A/WS/33, H1N1) infective activity. Furthermore, Applicants demonstrate herein that an alcoholic extract of goldenrod is more efficient at inhibiting viral infection than other types of extracts such as water extracts. A combination of these two plants (or specific parts or extracts thereof) provides an alternative way of attenuating/alleviating cold and flu symptoms and/or decreasing the duration of the infection period.

In addition to its capability to inhibit the influenza virus (e.g., common H1N1 strain as well as H1N1 Swine flu strain) in vitro infective activity, the combination of the present invention has been shown to be active in an in vivo animal model reproducing the influenza virus infection (Strain A/WS/33, H1N1).

Compositions

Accordingly, in a first aspect, the present invention presents a composition comprising a combination of ginger and goldenrod for the prevention and/or treatment of cold and/or flu infections (or associated symptoms).

In a specific embodiment of the composition of the present invention, the composition further comprises a carrier. In another embodiment of the composition of the present invention, the composition comprises a ginger extract and/or a goldenrod extract. In another embodiment, the combination comprises ginger powder. In another embodiment, the ginger extract is a crude ginger extract. In another embodiment, the ginger extract is a crude 100% water ginger extract. In another embodiment, the ginger extract is a $CO_2$ ginger extract. In another embodiment, the goldenrod extract is a crude goldenrod extract. In another embodiment, the goldenrod extract is a crude 100% water goldenrod extract. In another embodiment, the goldenrod extract is an alcoholic goldenrod extract. In another embodiment, the alcoholic goldenrod extract is a hydroalcoholic goldenrod extract. In another embodiment, the alcohol used for production of the hydroalcoholic extract comprises a primary alcohol. In another embodiment, the primary alcohol is methanol, ethanol, 1-propanol, 1-butanol or any combination thereof. In another embodiment, the primary alcohol used is ethanol. In another embodiment, the alcohol used for production of the hydroalcoholic extract comprises a secondary alcohol. In another embodiment, a mixture of at least two different alcohols is used. In another embodiment, the alcoholic extract is prepared using a solution comprising between about 20% and about 85% of alcohol. In another embodiment, the extract is prepared using a solution comprising 60% of alcohol. In another embodiment, the extract is prepared using a solution comprising about 30% of alcohol. In another embodiment, the combination comprises a ratio of between about 1:15 and about 10:1 of ginger:goldenrod. In another embodiment, the ratio is about 1:5 of ginger:goldenrod. In another embodiment, the ratio is about 5:1 of ginger:goldenrod. In another embodiment, the effective amount comprises between about 40 mg and about 4500 mg of ginger. In another embodiment, the composition comprises between about 40 mg and about 200 mg of ginger. In another embodiment, the composition comprises between about 43.5 mg and about 174 mg of ginger. In another embodiment, the composition comprises between about 1000 mg and about 4500 mg of ginger. In another embodiment, the composition comprises between about 2000 mg and about 4000 mg of ginger. In another embodiment, the composition comprises between about 200 mg and about 800 mg of goldenrod. In another embodiment, the composition comprises between about 400 mg and about 800 mg of goldenrod extract.

In another embodiment of the composition of the present invention, the composition comprises a blueberry powder. In another embodiment, the ginger is *Zingiber officinale* Roscoe. In another embodiment, the goldenrod is *Solidago virgaurea*. In another embodiment, ginger and goldenrod are the sole medicinal ingredients for the prevention or treatment of a cold or flu infection in the composition. In another embodiment, the composition further comprises as non-medicinal ingredients microcrystalline cellulose, cross-linked sodium carboxymethyl cellulose, stearic acid, silica colloidal, magnesium stearate and calcium monohydrogen phosphate.

In a related aspect, the present invention presents a nutraceutical and/or dietary composition (food supplement, beverage (e.g., 2-4 oz immune shot) or food) comprising a combination of ginger and goldenrod. In an embodiment, the composition is a nutraceutical or dietary or veterinary composition. In another embodiment, the composition is comprised in a beverage or food product. In another embodiment, the composition is comprised in a 2 to 6-oz shooter beverage. In another embodiment, the composition is adapted for administration within 48 h of the onset of cold or flu symptoms. In another embodiment, the composition is adapted for administration within 24 h of the onset of cold or flu symptoms. In another embodiment, the composition is adapted for administration twice daily.

In another embodiment of the composition of the present invention, the combination prevents or treats at least one of the following symptoms: the viral titer in the subject's blood or cells, runny nose, plugged nose, sneezing, sore throat, scratchy throat, cough, hoarseness, head congestion, chest congestion, exhaustion, fever, muscle pain, loss of appetite, headache and chills. In another embodiment, the combination prevents or treats at least two of the symptoms. In another embodiment, the combination of the present invention prevents, treats, or reduces at least 2 of the above symptoms.

In another embodiment of the composition of the present invention, the composition is for use in the prevention and/or treatment of cold and/or flu infection. In another embodiment, the combination prevents and/or treats the cold and/or flu infection synergistically. In another embodiment, the composition is for use in the prevention and/or treatment of an influenza infection. In another embodiment, the composition is for use in the prevention and/or treatment of a rhinovirus infection. In another embodiment, the composition is for the prevention of cold and/or flu infections. In another embodiment, the composition is for the treatment of cold and/or flu infections. In another embodiment, the composition is adapted for a veterinary application. In another embodiment, the composition is adapted for humans.

Methods

In another aspect, the present invention provides a method of preventing and/or treating a cold and/or flu infection in a subject in need thereof comprising administering to the subject an effective amount of a composition comprising a combination of ginger and goldenrod, whereby the cold or flu infection is prevented or treated.

In a specific embodiment of the method, the composition further comprises a carrier. In an embodiment the composition comprises a ginger extract and/or a goldenrod extract. In an embodiment, the composition comprises ginger powder. In an embodiment, the ginger extract is a crude ginger extract. In an embodiment, the ginger extract is a crude 100% water ginger extract. In an embodiment, the ginger extract is a $CO_2$ ginger extract. In an embodiment, the goldenrod extract is a crude goldenrod extract. In an embodiment, the goldenrod extract is a crude 100% water goldenrod extract. In an embodiment, the goldenrod extract is an alcoholic goldenrod extract. In an embodiment, the alcoholic goldenrod extract is a hydroalcoholic goldenrod extract. In an embodiment, the alcohol used for production of the hydroalcoholic extract comprises a primary alcohol. In an embodiment, the primary alcohol comprises methanol, ethanol, 1-propanol, 1-butanol or any combination thereof. In an embodiment, the primary alcohol is ethanol. In an embodiment, the alcohol used for production of the hydroalcoholic extract comprises a secondary alcohol. In an embodiment, a mixture of at least two different alcohols is used for production of the alcoholic extract. In an embodiment, the alcoholic extract is prepared using a solution comprising between about 20% and between about 85% of alcohol. In an embodiment, the alcoholic extract is prepared using a solution comprising about 60% of alcohol. In an embodiment, the alcoholic extract is prepared using a solution comprising about 30% of alcohol. In an embodiment, the composition comprises a ratio of between about 1:15 and about 10:1 of ginger:goldenrod. In an embodiment, the ratio is about 1:5 of ginger:goldenrod. In an embodiment, the ratio is about 5:1 of ginger:goldenrod. In an embodiment, the effective amount comprises between about 40 mg and about 4500 mg of ginger. In an embodiment, the effective amount comprises between about 40 mg and about 200 mg of ginger. In an embodiment, the effective amount comprises between about 43.5 mg and about 174 mg of ginger. In an embodiment, the effective amount comprises between about 1000 mg and about 4500 mg of ginger. In an embodiment, the effective amount comprises between about 2000 mg and about 4000 mg of ginger. In an embodiment, the effective amount comprises between about 200 mg and about 800 mg of goldenrod. In an embodiment, the effective amount comprises 400 mg and about 800 mg of goldenrod extract. In an embodiment, the composition further comprises a blueberry extract. In an embodiment, the ginger is *Zingiber officinale* Roscoe. In an embodiment, the goldenrod is *Solidago virgaurea*. In an embodiment, ginger and goldenrod are the sole medicinal ingredients for the treatment of cold and/or flu infections in the composition. In an embodiment, the composition further comprises as non-medicinal ingredients microcrystalline cellulose, cross-linked sodium carboxymethyl cellulose, stearic acid, silica colloidal, magnesium stearate and calcium monohydrogen phosphate. In an embodiment, the composition is a nutraceutical or dietary or veterinary composition. In an embodiment, the composition is a food supplement. In an embodiment, the composition is comprised in a beverage or food product. In an embodiment, the beverage is a 2 to 6 oz shooter beverage.

In another embodiment of the method of the present invention, the composition is administered within 48 h of the onset of cold or flu symptoms. In another embodiment, the composition is administered within 24 h of the onset of cold or flu symptoms. In another embodiment, the composition is administered twice daily. In another embodiment, the combination prevents and/or treats at least one of the following symptoms: the viral titer in the subject's blood or cells, runny nose, plugged nose, sneezing, sore throat, scratchy throat, cough, hoarseness, head congestion, chest congestion, exhaustion, fever, muscle pain, loss of appetite, headache and chills. In another embodiment, the combination prevents and/or treats at least two of the symptoms. In another embodiment, the combination prevents and/or treats the cold and/or flu infection synergistically.

In another embodiment of the method, the composition is for preventing and/or treating an influenza infection. In another embodiment of the method, the composition is preventing and/or treating a rhinovirus infection. In another embodiment of the method, the composition is for preventing cold and/or flu infections. In another embodiment of the method, the composition is for treating cold and/or flu infections. In another embodiment of the method, the subject is a non human animal. In another embodiment of the method, the subject is a human.

In accordance with another aspect of the present invention, there is provided a method of preventing and/or treating a cold and/or flu infection in a cell comprising contacting the cell with an effective amount of a combination of ginger and goldenrod, whereby the composition prevents and/or reduces the infective activity of a cold and/or flu virus. In accordance with another aspect of the present invention, there is provided a method of preventing and/or treating a cold and/or flu infection comprising administering a composition comprising a goldenrod alcoholic extract to a subject in need thereof, whereby the cold and/or flu infection is prevented and/or treated. In a specific embodiment, the above methods are for the prevention of a cold and/or flu infection.

In a further aspect, the present invention provides a method of preventing or treating a cold or flu infection in a cell comprising contacting the cell with an effective amount of a combination of ginger and goldenrod. In an embodiment, the combination prevents or reduces the infective activity of a cold or flu virus synergistically.

Uses

In a further aspect, the present invention concerns the use of a composition comprising a combination of ginger and goldenrod for the manufacture of a composition of the present invention for preventing or treating a cold or flu infection. In an embodiment, the use is for the manufacture of a medicament. In another embodiment, the use is for the manufacture of a nutraceutical or dietary composition (e.g., a food supplement or dietary supplement).

In a further aspect, the present invention concerns the use of the composition as defined above, for the prevention and/or treatment of a cold and/or flu infection or in the manufacture of a medicament, nutraceutical composition or dietary composition for the prevention and/or treatment of a cold and/or flu infection.

In a specific embodiment of the use of the present invention, the composition further comprises a carrier. In another embodiment, the composition comprises a ginger extract and/or a goldenrod extract. In another embodiment, the composition comprises ginger powder. In another embodiment, the ginger extract is a crude ginger extract. In another embodiment, the ginger extract is a crude 100% water ginger extract. In another embodiment, the ginger extract is a $CO_2$ ginger extract. In another embodiment, the goldenrod extract is a crude goldenrod extract. In another embodiment, the goldenrod extract is a crude 100% water goldenrod extract. In another embodiment, the goldenrod extract is an alcoholic goldenrod extract. In another embodiment, the alcoholic goldenrod extract is a hydroalcoholic goldenrod extract. In another embodiment, the alcohol used for production of the hydroalcoholic extract comprises a primary alcohol. In another embodiment, the primary alcohol comprises methanol, ethanol, 1-propanol, 1-butanol or any combination thereof. In another embodiment, the primary alcohol is ethanol. In another embodiment, the alcohol used for production of the hydroalcoholic extract comprises a secondary alcohol. In another embodiment, a mixture of at least two different alcohols is used for production of the alcoholic extract. In another embodiment, the alcoholic extract is prepared using a solution comprising between about 20% and between about 85% of alcohol. In another embodiment, the alcoholic extract is prepared using a solution comprising about 60% of alcohol. In another embodiment, the alcoholic extract is prepared using a solution comprising about 30% of alcohol. In another embodiment, the composition comprises a ratio of between about 1:15 and about 10:1 of ginger:goldenrod. In another embodiment, the ratio is about 1:5 of ginger:goldenrod. In another embodiment, the ratio is about 5:1 of ginger:goldenrod. In another embodiment, the effective amount comprises between about 40 mg and about 4500 mg of ginger. In another embodiment, the effective amount comprises between about 40 mg and about 200 mg of ginger. In another embodiment, the effective amount comprises between about 43.5 mg and about 174 mg of ginger. In another embodiment, the effective amount comprises between about 1000 mg and about 4500 mg of ginger. In another embodiment, the effective amount comprises between about 2000 mg and about 4000 mg of ginger. In another embodiment, the effective amount comprises between about 200 mg and about 800 mg of goldenrod. In another embodiment, the effective amount comprises 400 mg and about 800 mg of goldenrod extract. In another embodiment, the composition further comprises a blueberry extract. In another embodiment, the ginger is *Zingiber officinale* Roscoe. In another embodiment, the goldenrod is *Solidago virgaurea*. In another embodiment, ginger and goldenrod are the sole medicinal ingredients for the treatment of cold and/or flu infections in the composition. In another embodiment, the composition further comprises as non-medicinal ingredients microcrystalline cellulose, cross-linked sodium carboxymethyl cellulose, stearic acid, silica colloidal, magnesium stearate and calcium monohydrogen phosphate. In another embodiment, the composition is a nutraceutical or dietary or veterinary composition. In another embodiment, the composition is a food supplement. In another embodiment, the composition is comprised in a beverage or food product. In another embodiment, the beverage is a 2 to 6 oz shooter beverage. In another embodiment, the composition is adapted for administration within 48 h of the onset of cold or flu symptoms. In another embodiment, the composition is adapted for administration within 24 h of the onset of cold or flu symptoms. In another embodiment, the composition is adapted for administration twice daily. In another embodiment, the combination prevents and/or treats at least one of the following symptoms: the viral titer in the subject's blood or cells, runny nose, plugged nose, sneezing, sore throat, scratchy throat, cough, hoarseness, head congestion, chest congestion, exhaustion, fever, muscle pain, loss of appetite, headache and chills. In another embodiment, the combination prevents and/or treats at least two of the symptoms. In another embodiment, the combination prevents and/or treats the cold and/or flu infection synergistically. In another embodiment of the use, the composition is for preventing and/or treating an influenza infection. In another embodiment of the use, the composition is for preventing and/or treating a rhinovirus infection. In another embodiment of the use, the composition is for preventing cold and/or flu infections. In another embodiment of the use, the composition is for treating cold and/or flu infections. In another embodiment of the use, the composition is for use in a non human animal. In another embodiment of the use, the composition is for use in a human.

In another aspect, the present invention concerns a use of an effective amount of a combination of ginger and goldenrod for preventing and/or treating a cold and/or flu infection in a cell. In another aspect, the present invention concerns a use of a goldenrod alcoholic extract for preventing and/or treating a cold and/or flu infection. In an embodiment these uses are for the prevention of a cold and/or flu infection.

Kits

The present invention also provides a kit or commercial package for preventing or treating a cold or flu infection comprising a combination of ginger and goldenrod, together with instructions on how to prevent or treat a cold or flu infection.

In another aspect, the present invention concerns kit for preventing and/or treating a cold and/or flu infection comprising a the composition as defined herein, together with instructions to use the composition for preventing and/or treating a cold and/or flu infection or with methods or uses of the present invention as described herein.

Compositions, Methods, Uses and Kits

In an embodiment of the compositions, methods, uses and kits described above, the above-mentioned composition comprises ginger powder (i.e., ginger rhizome grinded and dried or lyophilized). In an embodiment, the above-mentioned composition comprises a ginger extract. In an embodiment, the extract is a crude extract of dried root. In an embodiment, the above-mentioned ginger extract is a $CO_2$ ginger extract. In another embodiment, the ginger extract is an alcoholic extract. Preferably, the ginger extract is a $CO_2$ ginger extract.

In an embodiment of the compositions, methods, uses and kits described above, the above-mentioned composition comprises goldenrod extract (i.e., whole goldenrod or parts thereof (e.g., flowers and/or leaves) grinded and dried or lyophilized). In an embodiment, the above-mentioned composition comprises the aerial part of goldenrod (whole or extract thereof). In an embodiment, the goldenrod extract is a $CO_2$ extract. In a preferred embodiment, the above-mentioned goldenrod extract is an alcoholic extract.

In an embodiment of the compositions, methods, uses and kits described above, the above-mentioned alcoholic extract is a hydroalcoholic extract. In an embodiment, the alcohol used for the production of the hydroalcoholic extract comprises a primary alcohol. Non-limiting examples of primary alcohols that may be used in accordance with the present invention include methanol, ethanol, 1-propanol, 1-butanol and a combination thereof. In an embodiment, the alcohol used for the production of the hydroalcoholic extract comprises a secondary alcohol. Non-limiting examples of secondary alcohols include 2-propanol, 2-butanol or a combination thereof. In an embodiment, the alcohol used for the production of the hydroalcoholic extract comprises a tertiary alcohol such as 2-methyl-2-propanol. In an embodiment, the alcohol used for the production of the hydroalcoholic extract comprises a polyhydric alcohol. Non-limiting examples of polyhydric alcohols include ethylene glycol, propylene glycol, diethylene glycol, dipropylene glycol, 1,3-butylene glycol, or a combination thereof. In a particular embodiment, the alcohol used for the production of the hydroalcoholic extract is ethanol.

In an embodiment of the compositions, methods, uses and kits described above, a mixture of at least two different alcohols is used for the production of the above-mentioned alcoholic extract.

In a particular embodiment of the compositions, methods, uses and kits described above, the above-mentioned alcoholic extracts of the present invention can be prepared using a solution comprising between about 20% and about 85% of alcohol. In an embodiment, the above-mentioned hydroalcoholic extract is prepared using a solution comprising about 30% of alcohol. In a specific embodiment, the hydroalcoholic extract is prepared using a solution comprising about 30% of ethanol.

In a particular embodiment of the compositions, methods, uses and kits described above, the composition of the present invention comprises a combination of ginger and goldenrod in such amounts and proportions so as to synergistically prevent or treat a cold or flu infection (e.g., so that it reduces the infective activity of the flu or cold virus at a level which is greater than the sum of the antiviral activity of each compound alone, for example in an in vitro assay for the inhibition of plaque forming unit).

In an embodiment of the compositions, methods, uses and kits described above, the combination comprises a ratio of between about 1:10 and 10:1 of ginger:goldenrod. In another embodiment, the ratio is about 1:5 of ginger:goldenrod. In a further embodiment, the ratio is about 5:1 of ginger:goldenrod. In a specific embodiment, the ratio between ginger powder and goldenrod hydroalcoholic extract used in the combination of the present invention is about 5:1 (ginger powder:goldenrod extract). In another particular embodiment, the ratio between ginger $CO_2$ extract and goldenrod hydroalcoholic extract used in the combination of the present invention is 1:5 (ginger extract:goldenrod extract).

In a particular embodiment of the compositions, methods, uses and kits described above, the above-mentioned composition comprises between about 40 mg and about 4500 mg (e.g., 40, 50, 60, 70, 80, 90, 100, 150, 200, 250, 300, 350, 400, 500, 600, 700, 800, 900, 1000, 1500, 2000, 3000, 3500, 4000, 4500 mg, etc.) of ginger powder and between about 200 mg and about 800 mg (e.g., 200, 300, 400, 500, 600, 700 mg) of goldenrod hydroalcoholic extract. In another embodiment, the above-mentioned composition comprises between about 2000 mg and about 4000 mg of ginger powder and between about 400 mg and about 800 mg of goldenrod alcoholic extract. In another particular embodiment, the above-mentioned composition comprises between about 40 mg and about 200 mg (e.g., 45, 60, 75, 90, 100, 120, 140, 150, 175 mg, etc.) of ginger $CO_2$ extract and between about 200 mg and about 800 mg of goldenrod hydroalcoholic extract. In a preferred embodiment, the above-mentioned composition comprises between about 43.5 mg and about 174 mg of ginger $CO_2$ extract and between about 200 mg and about 800 mg of goldenrod hydroalcoholic extract.

Although in particular embodiments of the compositions, methods, uses and kits described above, the composition of the present invention comprises certain amounts of ginger and goldenrod as defined above, the therapeutically effective amounts that should be administered for preventing or treating a cold or flu infection may be different. (e.g., if, for example, more than one capsule is administered or if the composition is administered more than once a day). Thus, in an embodiment, the effective amount or dose for preventing or treating a cold or flu infection comprises between about 40 mg and about 200 mg (e.g., 45, 60, 75, 90, 100, 120, 140, 150, 175 mg, etc.) of ginger $CO_2$ extract and between about 200 mg and about 800 mg (e.g., 200, 300, 400, 500, 600, 700 mg) of goldenrod hydroalcoholic extract daily. In another embodiment, the effective amount or dose for preventing or treating a cold or flu infection comprises between about 43.5 mg and about 174 mg of ginger $CO_2$ extract and between about 200 mg and about 800 mg of goldenrod hydroalcoholic extract daily. In yet another embodiment, the effective amount or dose for preventing or treating a cold or flu infection comprises between about 1000 and about 4000 mg (e.g., 1500, 2000, 3000, 3500, 4000 mg, etc.) of ginger powder and between about 200 mg and about 800 mg of goldenrod hydroalcoholic extract daily. In a further embodiment, the effective amount or dose for preventing or treating a cold or flu infection comprises between about 2000 and about 4000 mg (e.g., 1500, 2000, 3000, 3500, 4000 mg, etc.) of ginger powder and between about 200 mg and about 800 mg of goldenrod hydroalcoholic extract daily. In yet another embodiment, the effective amount or dose for preventing or treating a cold or flu infection comprises between about 2000 mg and about 4000 mg of ginger powder and between about 400 mg and about 800 mg of goldenrod hydroalcoholic extract.

The above-mentioned effective amounts of ginger and goldenrod may be administered in one or several doses. For example, compositions comprising about 43.5 mg of ginger $CO_2$ extract and about 200 mg of goldenrod hydroalcoholic extract may be administered 2 to 4 times a day. The skilled practitioner will know how to adapt the dosage in accordance with the age, sex and weight of the subject.

In particular embodiment of the compositions, methods, uses and kits described above, the composition of the present invention may comprise additional products or extracts for preventing or treating any symptoms of a cold or flu infection or may be used in combination with any additional cold or flu medicine. Non-limiting examples of additional cold or flu medicines include Cold Fx™, Tamiflu™, *Echinacea*, ginseng, amantadine, rimantadine, vitamin C, etc. In a particular embodiment, the composition of the present invention further comprises a blueberry powder. In another particular embodiment, the composition of the present invention comprises as sole medicinal ingredients for the prevention or treatment of a cold or flu infection a combination of ginger and goldenrod. In another embodiment of the present invention, the composition of the present invention comprises extracts from five different plants including extracts from ginger and goldenrod as sole herbal extracts or as sole medicinal ingredients. In a more specific embodiment, the composition of the present invention comprises extracts from four different plants including extracts from ginger and goldenrod as sole herbal extracts or as sole medicinal ingredients. In a more specific embodiment, the composition of the present invention comprises extracts from three different plants including extracts from ginger and goldenrod as sole herbal extracts or as sole medicinal ingredients. In a more specific embodiment, the composition of the present invention comprises extracts from ginger and goldenrod as sole herbal extracts.

In addition to medicinal ingredients for the prevention or treatment of a cold and/or flu infection, the composition of the present invention may comprise additional non-medicinal ingredients. For example, preparations to be administered orally can contain one or more additives such as sweeteners, aromatizing agents, colorants, stabilizing agents and preservatives (e.g., antimicrobial agents). The composition of the present invention can be mixed with customary pharmaceutically acceptable carriers or vehicles, as for example inert diluents. In a particular embodiment, the composition of the present invention additionally comprises at least one (or two, or three, or four, etc.) of the following non-medicinal ingredients: microcrystalline cellulose, cross-linked sodium carboxymethyl cellulose, Stearic acid, Silica colloidal, Magnesium stearate, Calcium monohydrogen phosphate and Lecithin.

Any species of goldenrod and ginger may be used in accordance with the present invention. In an embodiment, the goldenrod species is *Solidago decurrense, Solidago canadensis, Solidago virgaurea* or any combination thereof. In a specific embodiment, the goldenrod species is *Solidago virgaurea* and the ginger species is *Zingiber officinale Roscoe*.

Other objects, advantages and features of the present invention will become more apparent upon reading of the following non-restrictive description of specific embodiments thereof, given by way of examples only with reference to the accompanying drawings.

DESCRIPTION OF ILLUSTRATIVE EMBODIMENTS

Figure 1:
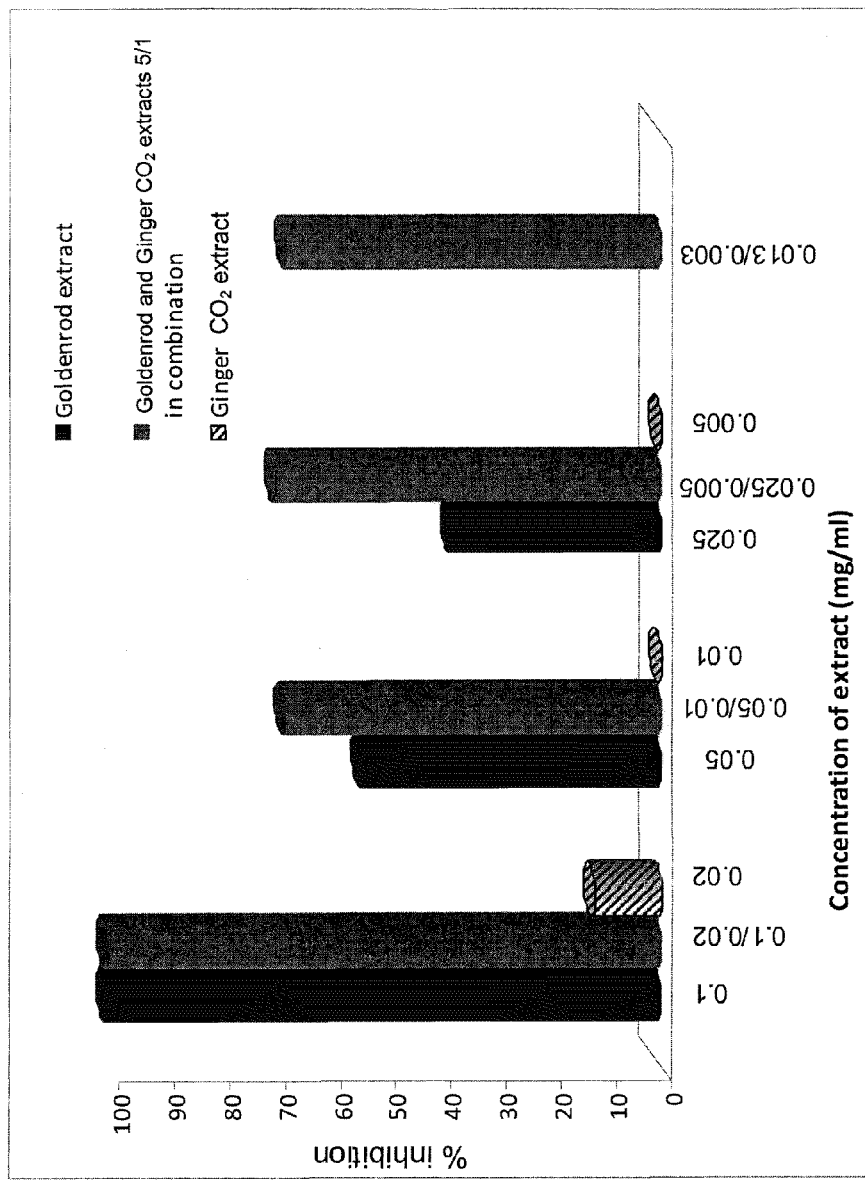
FIG. 1 shows the inhibitory (antiviral) effect of ginger $CO_2$ extract, goldenrod extract (ETOH) and a combination thereof on Influenza virus capacity to infect (Plaque Forming Unit) an MDCK cell monolayer.

The present Applicants have surprisingly discovered that a combination of ginger and goldenrod acts synergistically to reduce the infective activity of cold and/or flu virus, thereby reducing the progression of the infection, viral titer and associated symptoms. Thus, the present invention is concerned with the use of a combination of ginger and goldenrod acting together to prevent or treat a cold or flu infection as well as compositions and methods derived therefrom for treatment.

As used herein, the terms "treat/treating/treatment" and "prevent/preventing/prevention", refer to eliciting the desired biological response, i.e., a therapeutic and prophylactic effect, respectively. In accordance with the subject invention, the therapeutic effect comprises a decrease/reduction in the progress of the infection or in the severity or number of associated symptoms or a complete cure of the infection and/or associated symptoms. In accordance with the invention, a prophylactic effect may comprise a delay or decrease/reduction in the onset of, progression of infection, or the severity or number of associated symptoms (e.g., viral titer in the subject's blood or cells, runny nose, plugged nose, sneezing, sore throat, scratchy throat, cough, hoarseness, head congestion, chest congestion, feeling tired, fever, muscle pain, loss of appetite, headache and chills) following administration of a combination/composition of the present invention. In an embodiment, the composition of the present invention, comprising a combination of goldenrod and ginger, completely prevents the subject from contracting a cold or flu infection. The methods, compositions, formulations and uses described herein are suitable for both humans and animals (including birds), preferably mammals.

Animals can benefit from the compositions, methods, uses and kits of the present invention. For example, swine flu and avian flu are major problems in the swine, poultry and cattle industries. Recently, two pandemic strains of influenza, H1N1 (swine flu) and H5N1 avian flu affected this industry resulting in significant losses for producers. Available preventive therapies such as vaccine are too costly for extensive use. A natural and antibiotic free treatment such as a phytoremedy, would likely enable a better control of rhinovirus and influenza infection and increase gains of the livestock industry. Other animals (e.g., herd animals including horse, sheep, goats, etc.; and pets such as dogs, cats, etc.) are also prone to flues and would benefit from a preventive treatment or early treatment.

Thus, as used herein, the term "subject" in the context of veterinary application of the present invention relates to any mammal including swine, lamb, goat, cow (e.g., beef, veal), bird (e.g., chicken, duck, goose), mouse, rat, monkey, cat, dog, and a horse. In another specific embodiment, it refers to a human. A "subject in need thereof" or a "patient" in the context of the present invention is intended to include any subject that will benefit or that is likely to benefit from the combination of ginger and goldenrod of the present invention. In an embodiment, a subject in need thereof is a subject diagnosed with cold or flu. In another embodiment, a subject in need thereof is a subject that is likely to catch the cold or the flu or in which a cold or flu infection is likely to have important health consequences (e.g., young children, elderly or immune deficient subjects, members of herds where at least one animal shows symptoms of infections, etc.). The likelihood of contracting cold or flu can be determined for instance with the prevalence of the disease in the subject's environment including close members of the family (sisters, brothers, parents, grand-parents, uncles and aunts, spouse, colleagues, friends, etc.), members of herds. In an embodiment, a subject in need thereof is a subject suffering from the cold or the flu or any associated symptom.

As used herein, the term "synergistically" means that two or more substances work together in a cooperative manner so the total effect of the combination is greater than the sum of each of the substances taken individually. Accordingly, the expression "synergistically prevents or treat" a cold or flu infection or associated symptoms means that the combination of the present invention is more effective in reducing the infective activity of the cold or flu, or in relieving an associated symptom, than the sum of the effects of each of goldenrod and ginger acting individually. This includes decreasing the time for recovery or increasing the speed at which symptoms are alleviated or reduced. A synergistic effect is present if, for example, the inhibition of the virus infective activity/capacity (e.g., reduction in the number of plaque forming units (PFU) in infected cell culture) following treatment with a combination of goldenrod and ginger is 80%, while the inhibition of the virus infective activity/capacity following treatment with goldenrod alone is 25% and that of ginger alone is 30% (80% being greater than 25%+30%).

As used herein, the term "cold" refers to a contagious viral infectious disease of the upper respiratory system mostly caused by picornaviruses (including rhinoviruses) or coronaviruses. It also includes infections by parainfluenza viruses, human respiratory syncytial virus, adenoviruses and enteroviruses. Common symptoms of cold include sore throat, runny nose, nasal congestion, cough and sneezing.

As used herein, the term "flu" refers to an infectious disease caused by a RNA virus from the Orthomyxoviridae (influenza virus) family. It affects birds and mammals. Common symptoms of flu include chills, fever, sore throat, scratchy throat, muscle pains, headache, chest congestion, head congestion, coughing, weakness, exhaustion, loss of appetite and general discomfort.

The articles "a," "an" and "the" are used herein to refer to one or to more than one (i.e., to at least one) of the grammatical objects of the article.

The terms "including" and "comprising" are used herein to mean, and are used interchangeably with, the phrases "including but not limited to" and "comprising but not limited to".

The terms "such as" is used herein to mean, and is used interchangeably herein with "such as but not limited to".

Extracts

The two main active/medicinal components of the combination of the present invention are ginger and goldenrod, parts thereof or extracts thereof. In accordance with the present invention, whole ginger root (rhizome) or whole goldenrod reduced to powder (e.g., grinded and dried or lyophilized) can be used in the combination of the present invention. Alternatively, ginger root extract or goldenrod extract can be used. The extract may be from the whole plant or from a part thereof (e.g., the aerial part of goldenrod). In an embodiment, the ginger extract and/or the goldenrod extract is a crude extract (e.g., crude 100% water extract).

As used herein, the term "crude" in the expression "crude extract" refers to an unfractionated water extract (e.g., from ginger or goldenrod). A crude extract may be a water concoction or brew of any type wherein ginger root or goldenrod is cut into pieces and/or grinded, optionally lyophilized and mixed with water to obtain a water extract which can be optionally filtered prior to use.

Alternatively, an alcoholic extract or $CO_2$ supercritical extract can be used in accordance with the present invention. The goldenrod and ginger extracts used in accordance with the present invention may be home made or laboratory made or may be extracts which are commercially available such as ginger and goldenrod extracts available from Martin Bauer (Italy), Flavex (Germany) or Finzelberg (Germany). In a preferred embodiment, the ginger extract is a $CO_2$ extract obtained from *Zingiber officinale* root, and the goldenrod extract is a hydroalcoholic extract obtained from the aerial part of *Solidago virgaurea*.

A number of standard extraction techniques known in the art can be used to prepare the plant extracts of the present invention. In general, the extraction process entails contacting solid plant material with a solvent with adequate mixing and for a period of time sufficient to ensure adequate exposure of the solid plant material to the solvent such that desired therapeutic activity (bioactive components) present in the plant material can be taken up by the solvent.

As indicated above, the plant material is derived from one or a combination of the species of ginger and goldenrod. Non-limiting examples of goldenrod species that may be used in accordance with the present invention include *Solidago albopilosa, Solidago altiplanities, Solidago arguta, Solidago auriculata, Solidago bicolor, Solidago brachyphylla, Solidago buckleyi, Solidago caesia, Solidago calcicola, Solidago californica, Solidago canadensis, Solidago cutleri, Solidago deamii, Solidago decurrense, Solidago discoidea, Solidago fistulosa, Solidago flaccidifolia, Solidago flexicaulis, Solidago gattingeri, Solidago gigantea, Solidago glomerata, Solidago gracillima, Solidago guiradonis, Solidago hispida, Solidago juliae, Solidago juncea, Solidago latissimifolia, Solidago leavenworthii, Solidago ludoviciana, Solidago macrophylla, Solidago missouriensis, Solidago mollis, Solidago multiradiata, Solidago nana, Solidago nemoralis, Solidago odora, Solidago ouachitensis, Solidago patula, Solidago petiolaris, Solidago pinetorum, Solidago plumosa, Solidago porteri, Solidago puberula, Solidago pulchra, Solidago radula, Solidago roanensis, Solidago rugosa, Solidago rupestris, Solidago sciaphila, Solidago sempervirens, Solidago shortii, Solidago simplex, Solidago simulans, Solidago speciosa, Solidago spectabilis, Solidago spathulata, Solidago sphacelata, Solidago spithamaea, Solidago squarrosa, Solidago stricta, Solidago tortifolia, Solidago tenuifolia, Solidago uliginosa, Solidago Solidago velutina, Solidago verna, Solidago virgaurea* and *Solidago wrightii*. Preferably, the species of goldenrod is *Solidago decurense, Solidago canadensis, Solidago virgaurea* or a mixture thereof. In a particular embodiment, the goldenrod species is *Solidago virgaurea*.

The plant material employed in the extraction process can be the entire plant or it can be one or more distinct tissues from the plant or plants, for example, leaves, roots, the aerial part such as flowers and stems, etc. If desired, the plant material can be treated in order to facilitate the extraction process. Typically such treatment results in the plant material being fragmented by some means such that a greater surface area is presented to the solvent. For example, the plant material can be crushed or sliced mechanically, using a grinder or other device to fragment the plant parts into small pieces or particles, or the plant material can be frozen in liquid nitrogen and then crushed or fragmented into smaller pieces.

The solvent extraction process employed in the preparation related to the invention typically employs as solvent an aqueous solvent (such as water or a buffer), a liquid organic compound, or a combination thereof. Of course, all of the reagents used for the extraction process must be acceptable for use in humans and other animals or if not, the purification process must ensure that the purified extract is free of any toxic impurities prior to human consumption. Exemplary liquid organic compounds that can be used as solvents in the extraction process to prepare extracts include, but are not limited to, alcoholic solvents, which include primary alcohols such as methyl alcohol (methanol), ethyl alcohol (ethanol), 1-propanol and 1-butanol; secondary alcohols such as 2-propanol and 2-butanol; tertiary alcohols such as 2-methyl-2-propanol, and liquid polyhydric alcohols such as glycerin and glycols. Suitable glycols include, for example, ethylene glycol, propylene glycol, diethylene glycol, dipropylene glycol and 1,3-butylene glycol. Other known organic solvents for plant extraction include acetone, tetrahydrofuran, acetonitrile, 1,4-dioxane, pyridine, dimethylsulfoxide, N,N-dimethyl formamide, acetic acid, diethyl ether and ethyl acetate.

Supercritical extraction can also be used in the preparation of an extract of the present invention. It uses $CO_2$ as a solvent. Under pressure at a temperature below 40° C., $CO_2$ is in its supercritical state, i.e., liquid. It gains the quality of a solvent with the fluidity of a gas. Generally, the $CO_2$ extraction equipment is composed of a $CO_2$ working tank filled with liquid $CO_2$ at ambient temperature, a pump for increasing pressure and driving the circulation, an extractor which contains the powdered raw material, an expansion valve and a separator for collecting the extract. In addition, there are different heat exchangers for adjusting the temperature conditions of the circulating gas. Under supercritical conditions established in the extractor, $CO_2$ has solvent properties for lipophilic ingredients (e.g., gingerols and shogaols in ginger) whereas $CO_2$ is in the gas phase without solvent power under the conditions in the separator (e.g., 60 bar, 30° C.). Thus, the extract is precipitated and the gas is regenerated. The $CO_2$ is then liquefied by cooling and given back into the working tank which completes the $CO_2$ cycle.

A variety of conditions can be employed for the extraction process. Typically, the extraction procedures are conducted over a period of time between about 10 minutes and about 72 hours at a temperature between about 4° C. and about 50° C. However, temperatures between about 4° C. and about 90-100° C., for example between about 4° C. and about 70° C., can be employed. Similarly, the extraction time may be varied depending on other extraction conditions, such as the solvent and temperature employed; for example, the extraction time can range from several minutes to several days. Determination of appropriate extraction temperatures and times is within the ordinary skills of a worker in the art.

Adequate contact between the solvent and the plant material can be encouraged by shaking the suspension. Alternatively, an extraction device equipped with, for instance, a stirring machine, can be employed, which may improve the extraction efficiency. The extraction can be carried out at under atmospheric pressure, under pressure (i.e., above atmospheric pressure) or at reduced pressure (below atmospheric pressure) established by, for example, aspiration (vacuum). Appropriate extraction conditions can readily be determined or selected by one skilled in the art taking into consideration the production conditions such as production facilities and yields.

The present invention contemplates that the extraction process may be carried out on various scales including known large, medium and small-scale methods of preparing extracts.

Following the extraction process, the liquid fraction (the extract) can be separated from the solid (insoluble) matter. Separation of the liquid and solid fractions can be achieved by one or more standard separation processes known to those skilled in the art, such as various centrifugation or filtration processes. In one embodiment of the invention, the extract is separated from solid matter after the extraction by one or more filtration steps. In another embodiment, the extract is separated from solid matter after the extraction by a series of filtration steps.

In an embodiment, the ginger $CO_2$ extract is an essential oil obtained by $CO_2$ extraction (also known as supercritical extraction or supercritical fluid $CO_2$ extraction) using organic ginger (rhizome or underground part of *Zingiber officinale* Roscoe). In a specific embodiment, the ginger $CO_2$ extract comprised in the combination of the present invention is obtained from very well documented plant material and is standardized for its general chemical fingerprint including the identification of specific marker compounds (gingerols and shogaols). In an embodiment, the type of ginger extract comprised in the combination of the present invention is 20-25 times concentrated in pungent compounds (Shogaols and gingerols) compared to the original plant material. An example of such an extract is from Flavex (Germany).

In an embodiment, the goldenrod extract is a dried concentrated extract obtained by extraction with a mix of water and alcohol of between about 20% and about 85% (e.g., 25, 30, 35, 40, 45, 50, 55, 60, 65, 70, 75, 80, 85%) alcohol:water. In an embodiment, the goldenrod extract is a dried 5-7:1 concentrated extract obtained by extraction with a mix of 70% water and 30% alcohol. In a particular embodiment, the alcohol is ethanol. In an embodiment, it contains 90% of the native extract and 10% of precipitated silica DAB (Deutsche Arzneibuch). In a specific embodiment, the goldenrod extract comprised in the combination of the present invention is a commercial extract obtained from very well documented plant material standardized for its general chemical fingerprint including the identification of specific marker compounds (flavonoids, available for example from Finzelberg (Germany)).

Table I summarizes the main characteristics of the $CO_2$ and hydroalcoholic extracts used in particular embodiments of the present invention.

TABLE I

Characteristics of two exemplary ginger or goldenrod-based active extracts of the present invention

| Active agent | Plant origin | Extract type | Extract form | Chemical marker compounds |
|---|---|---|---|---|
| Ginger $CO_2$ extract (e.g., from Flavex, Germany) | *Zingiber officinale* (dried organic rhizome) | Supercritical $CO_2$ extract | Liquid | Gingerols and shogaols |
| Goldenrod extract (e.g., from Finzelberg, Germany) | *Solidago virgaurea* L. (dried aerial part) | Crude hydroalcoholic extract (30:70, ethanol:$H_2O$) | Dry | Flavonoids |

Formulations

The compositions of the present invention comprising a combination of ginger, goldenrod, parts thereof or extracts thereof may be formulated in various ways according to the route of administration. The compositions of the present invention may be administered in any suitable way including for example topically (local effect, substance is applied directly where its action is desired, e.g., nasally) or orally (e.g., sublingual). Administration is carried out in a customary manner, preferably orally.

The route of administration can depend on a variety of factors, such as the environment and therapeutic goals, and particulars about the subject. Thus, the compositions of the present invention can be formulated in any desired way, e.g., in or as a feed, a food (e.g., spice, animal feed, etc.), a liquid (e.g., a syrup or an immune shot such as a 2-4 oz single shot), a cream, an aerosol, a spray, a tablet, dried powder, dried plants, a capsule, a gel, a nanosuspension, a microgel or a suppository. The preferred route of administration is orally, in the form of a capsule, tablet, or the like or as a liquid formulation such as a beverage (e.g., a 2-4 oz immune shot comprising extracts from ginger and goldenrod). The composition of the present invention may also be supplied as a mixture of goldenrod and ginger extracts in the form of a powder which can later be mixed with water or any other suitable liquid beverage or food.

In accordance with the present invention, ginger and goldenrod or their extracts can be mixed with customary pharmaceutically acceptable carriers, diluents or vehicles and, if appropriate, with other auxiliary molecules.

As indicated above, the composition may further comprise a pharmaceutically/nutraceutically acceptable carrier or excipient. As used herein "pharmaceutically acceptable carrier" or "excipient" includes any and all solvents, buffers, dispersion media, coatings, antibacterial and antifungal agents, isotonic and absorption delaying agents and the like that are physiologically compatible. The carrier is selected for administration by the chosen route of administration. The use of such media and agents/excipients/carriers/non-medicinal ingredients for pharmaceutically active substances is well known in the art (Rowe et al., Handbook of pharmaceutical excipients, 2003, 4th edition, Pharmaceutical Press, London UK). Except insofar as any conventional media or agent is incompatible with the active compound, use thereof in the pharmaceutical/nutraceutical/dietary compositions of the invention is contemplated.

Non-limiting pharmaceutically suitable materials that may be incorporated in pharmaceutical/nutraceutical/dietary preparations of the present invention include preservative agents, solubilising/diluting agents/solvents, antioxidants, enteric coatings, absorption enhancers, pH adjusting agents and buffers, dispersing agents, coatings, antibacterial and antifungal agents, absorption delaying agents (controlled time-release), osmolarity adjusters, isotonic agents, preservative agents, stabilizers, surfactants, thickening agents, solvents, emollients, coloring agents, wetting agents, as well as colors and flavors. Methods for preparing appropriate formulations are well known in the art (see e.g., Hendrickson, 2005).

The expression "preservative agent" as used herein is meant to refer to any ingredient capable of retarding or preventing microbial or chemical spoilage and protecting against discoloration. Without being so limited, they include benzalkonium chloride, benzethonium chloride, benzyl alcohol, butylparaben, chlorobutanol, chlorocresol, cresol, ethylparaben, methylparaben, myristyl gamma-picolinium chloride, phenol, phenoxyethanol, phenylmercuric acetate, phenylmercuric nitrate, propylparaben and thimerosal (see Nema, 1997).

The term "solvent" as used herein is meant to refer to ingredients capable of facilitating the solubilization of an active ingredient within the formulation. Without being so limited, it includes water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

The oral formulation can be administered in the form of granules, powder, capsules, pills, tablets, film-coated tablets, sugar-coated tablets, syrups, emulsions, suspensions, dispersions, aerosols, solutions, lozenges and/or liquids. In an embodiment, the composition of the present invention is formulated in the form of a capsule. It can also be administered as suppositories, vaginal suppositories, and/or parenterally, e.g., in the form of solutions, emulsions, creams or suspensions. It can be administered in preparation for time delayed release, or protected from gastric acid by coating in order to be released in the intestinal part of the gut.

Capsules can contain the composition as a single constituent or mixed with a solid diluent such as calcium carbonate, calcium phosphate or kaolin.

The composition according to the invention can be formulated as liquid, pasty or solid preparations, for example as aqueous or alcoholic solutions, aqueous suspensions or emulsions.

Aqueous solutions suitable for oral use are prepared by dissolving the active compound(s)/composition(s) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. Examples of non-aqueous solvents are alcohol, benzyl benzoate, butyl alcohol, polyethylene glycol, propylene glycol, N,N dimethylacetamide, ethyl oleate, oleyl oleate, glyceryl trioleate, glyceryl dioleate, glyceryl monooleate, cetyl alcohol, stearyl alcohol, capric acid, undecenoic acid, undecanoic acid, lauric acid, oleic acid, synthetic glycerides of saturated fatty acids with 8 to 12 carbon atoms, polyoxyethylene derivatives of glycerol, beeswax, glycerine, mineral oil, vegetable oil such as but not limited to corn oil, cottonseed oil, peanut oil, canola oil, sesame oil, safflower oil, soybean oil, arachis oil, castor oil, linseed oil, soya bean oil, sunflower seed oil, olive oil, fish liver oil, and any combination thereof (see Nema, 1997).

Tablet forms can include one or more of lactose, sucrose, mannitol, sorbitol, calcium phosphates, corn starch, potato starch, microcrystalline cellulose, cross-linked sodium carboxymethyl cellulose, colloidal silica, gelatin, colloidal silicon dioxide, talc, calcium monohydrogen phosphate, magnesium stearate, stearic acid, and other excipients, colorants, fillers, binders, diluents, buffering agents, moisturizing agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Enteric coatings can further be used on capsules of the present invention to resist prolonged contact with the strongly acidic gastric fluid, but dissolve in the mildly acidic or neutral intestinal environment. Without being so limited, cellulose acetate phthalate, Eudragit™ and hydroxypropyl methylcellulose phthalate (HPMCP) can be used in enteric coatings of compositions of the present invention. Cellulose acetate phthalate concentrations generally used are 0.5-9.0% of the core weight. The addition of plasticizers improves the water resistance of this coating material, and formulations using such plasticizers are more effective than when cellulose acetate phthalate is used alone. Cellulose acetate phthalate is compatible with many plasticizers, including acetylated monoglyceride; butyl phthalybutyl glycolate; dibutyl tartrate; diethyl phthalate; dimethyl phthalate; ethyl phthalylethyl glycolate; glycerin; propylene glycol; triacetin; triacetin citrate; and tripropionin. It is also used in combination with other coating agents such as ethyl cellulose, in drug controlled-release/time-release preparations.

In an embodiment, the compositions comprising the combination of ginger and goldenrod of the present invention can be formulated for administration as foods or dietary supplements using one or more consumable carriers. A "consumable carrier" is herein defined as any food, food ingredient, or food additive or any excipient utilized for tabletting, encapsulation, or other formulation of an active agent for oral administration, whether for human or animal/veterinary use. For dietary supplements, the combination of the present invention can be mixed according to routine methods in the art. Dietary supplements can be prepared in a variety of forms including, but not limited to, liquid, powder or solid pill form. The extract or composition of the present invention can be administered either alone or in combination with other compounds or extracts including where combining compounds or extracts would lead to additive or synergistic effects. The extract and/or composition of the present invention can also be added directly to foods and ingested as part of a normal meal. Various methods are known to those skilled in the art for addition or incorporation of such agents into foods.

Dosage

Compositions and formulations of the present invention are administered in amounts and at a frequency sufficient to prevent and/or treat colds and/or flu infections and/or ameliorate any symptoms associated with cold and/or flu.

Any amount of a composition of the present invention can be administered to a subject, provided it is not associated with important adverse effects and it is in a non-toxic dose. The dosages may depend on many factors including the mode of administration, the age and sex of the subject. Other factors, such as the general health and condition of the subject as well as medications currently taken by the subject may modify the dosage of the compositions of the present invention. Typically, the amount of goldenrod and ginger (or their extracts) contained within a single dose will be an amount that effectively prevents or treats a cold or flu infection and one or more associated symptoms, without inducing significant toxicity, i.e., the composition improves or reduces one or more of: viral titers in the subject's blood or cells, runny nose, plugged nose/nasal congestion, sneezing, sore throat, scratchy throat, cough, hoarseness, head congestion, chest congestion, general weakness, fever, muscle pain, loss of appetite, headache and chills. Generally, the effective dose will not exceed CA, US and EP pharmacopeia for each product individually.

Thus, in one aspect of the present invention, the composition (food supplement or food stuff) comprising ginger and goldenrod or extracts thereof is administered prior to the onset of cold and/or flu symptoms as a preventive measure. In another aspect of the present invention, the pharmaceutical or nutraceutical or dietary composition of the present invention is administered in combination with a drug or drugs used to treat cold and/or flu symptoms. In a further aspect, the composition of the present invention is administered once the subject has been diagnosed with a cold or flu infection or after the onset of cold or flu symptoms. In another embodiment, the composition of the present invention is administered in combination with one or more other drugs used for the prevention and/or treatment of cold and/or flu infections such as Cold Fx™, Tamiflu™, *Echinacea*, ginseng, amantadine, rimantadine, Vitamin C, etc.

As used herein the expression "effective amount" or "therapeutically effective amount" is meant to refer to an amount effective to achieve the desired therapeutic effect such as an improvement of the condition of the patient, while avoiding adverse side effects. An effective amount can be administered in one or more doses. For the purposes of this invention, an effective amount of the composition of the present invention is an amount that induces a therapeutic or prophylactic response against cold and/or flu infections. Such amount may vary according to the nature of the infection (specific type of viral infection), the severity of the infection, the mode of administration, the age, weight and sex of the affected subject, etc. One skilled in the art can easily and without difficulty determine such an effective amount. Generally, the effective amount will be between about 40 mg and about 4500 mg of ginger of ginger (e.g., $CO_2$ extract) and about 200 mg and about 800 mg of goldenrod (e.g., hydroalcoholic extract). In an embodiment, the effective amount is between about 43.5 mg and about 174 mg of ginger $CO_2$ extract and between about 200 mg and about 400 mg of goldenrod hydroalcoholic extract. In another embodiment, the above-mentioned composition comprises between about 1000 mg and about 4500 mg of ginger powder and between about 200 mg and about 800 mg of goldenrod alcoholic extract. In an embodiment, the above-mentioned composition comprises between about 2000 mg and about 4000 mg of ginger powder and between about 400 mg and about 800 mg of goldenrod alcoholic extract.

In a related aspect of the present invention, the ratio between the amount of ginger and goldenrod is adjusted so as to obtain an antiviral synergistic effect (i.e., an effect on the inhibition of viral infection that is greater than the sum of the effects observed with ginger and goldenrod when administered alone). The ratio will be adapted depending on the type of extract that is used. In an embodiment, the ratio between ginger powder and goldenrod alcoholic extract is between about 10:1 and about 5:3 (e.g., 8:1, 7:1, 6:1, 5:1, 5:2, etc.) of ginger powder:goldenrod alcoholic extract. Preferably, the ratio is about 5:1 of ginger powder:goldenrod alcoholic extract. In another embodiment, the ratio between ginger $CO_2$ extract and goldenrod alcoholic extract is between about 1:15 and about 3:5 (e.g., 1:10, 1:8, 1:7, 1:6, 1:5:, 2:5, etc.) of ginger $CO_2$ extract:goldenrod alcoholic extract. Preferably, the ratio is about 1:5 of ginger $CO_2$ extract:goldenrod alcoholic extract.

The effective amount may be given daily in a single or several doses (e.g., single daily dose, twice daily, three times per day or 4 times per day). It may also be given every 2 days, every 3 days or once a week, as prescribed. Preferably, the effective amount is given twice daily.

The effective amount to be administered to a human subject may be calculated from studies in animals. The dose may be scaled up to a human equivalent dose (HED) for starting clinical trials using published conversion tables which provide a conversion factor from mice to human.

These are simply guidelines since the actual dose must be carefully selected and titrated by the attending physician based upon clinical factors unique to each patient. The optimal daily dose will be determined by methods known in the art and will be influenced by factors such as the age of the patient as indicated above and other clinically relevant factors.

The present invention is illustrated in further details by the following non-limiting examples.

Example 1

In Vitro Synergistic Antiviral Activity of a Combination Comprising Ginger and Goldenrod Extracts Against Influenza Virus Infection Applicants have demonstrated that ginger and goldenrod extracts alone, as well as their combination, show antiviral activity in a cellular model recognized as a standard way to analyze antiviral activity of therapeutic products (Hayden F, 1980). This model uses a monolayer MDCK (Madin-Darby Canine Kidney) cell line that is infected with an influenza virus (Influenza A/WS/33, H1N1), resulting in lysis plaques (infected cells area) that are then counted. In this analytical model, in presence of antiviral agents, the number of lysis plaques is decreased proportionally to the antiviral power of the tested agents.

Monolayers of MDCK cells (ATCC#CCL-34) were grown in 6-well culture plates until confluency. Before the infection or inoculation, the media was removed and cells were washed delicately twice with pre-warmed DMEM without any additives. 200 μl of product (goldenrod (*Solidago virgaurea*) ETOH Hydroalcoholic extract from Finzelberg, product No. 0193305 and/or ginger (*Zingiber officinale*) $CO_2$ extract from Flavex product code 0.14.013) were added at proper dilution in DMEM with TPCK (Trypsin treated with L-1-Tosylamido-2-phenylethyl chloromethyl ketone to reduce chymotrypsin activity without affecting trypsin activity) 2 μg/ml. Cells were infected with the human influenza virus A/WS/33 (ATCC #VR-1520), H1N1, diluted in serum-free DMEM with TPCK in 200 μl. The plates were incubated for an hour at room temperature. After adsorption, the cells were overlaid with 3 ml of a 0.6% agarose in pre-defined media containing the product and TPCK 2 μg/ml. Vehicle was used as control. All assays were done in duplicate. Once overlaid the plates were incubated at 37° C., 5% $CO_2$ in a humidified atmosphere for 48-72 hours.

After the incubation, the plates were stained with Neutral Red. All wells were digitally photographed and plaques were counted and the plaque inhibition for each dilution of product was calculated.

The inhibition is reported as percentage (%) of inhibition of infection as compared with infection in the absence of a product. Percentage inhibition was calculated according to the formula:

$$\text{Percentage (\%) inhibition} = [C_A - C_B / C_A] \times 100$$

wherein $C_A$ is the number of plaques in the absence of a product or plant extract and $C_B$ is the count of plaques in the presence of the extract.

The goldenrod extract was shown to inhibit the influenza viral infection by 50% at a concentration of 0.04 mg/ml according to the curve obtained with data (not shown). The ginger $CO_2$ extract was shown to inhibit the viral infection at concentrations higher than 0.05 mg/ml according to the curve obtained with data (not shown), and the mix 5/1 (goldenrod/ginger $CO_2$) was shown to inhibit the viral infection by 68% at a concentration of 0.013/0.003 mg/ml. These results clearly reflect the synergic effect of the goldenrod and ginger $CO_2$ extracts when mixed together in a ratio of 5/1 (goldenrod: ginger, see also FIG. 1).

Figure 2:
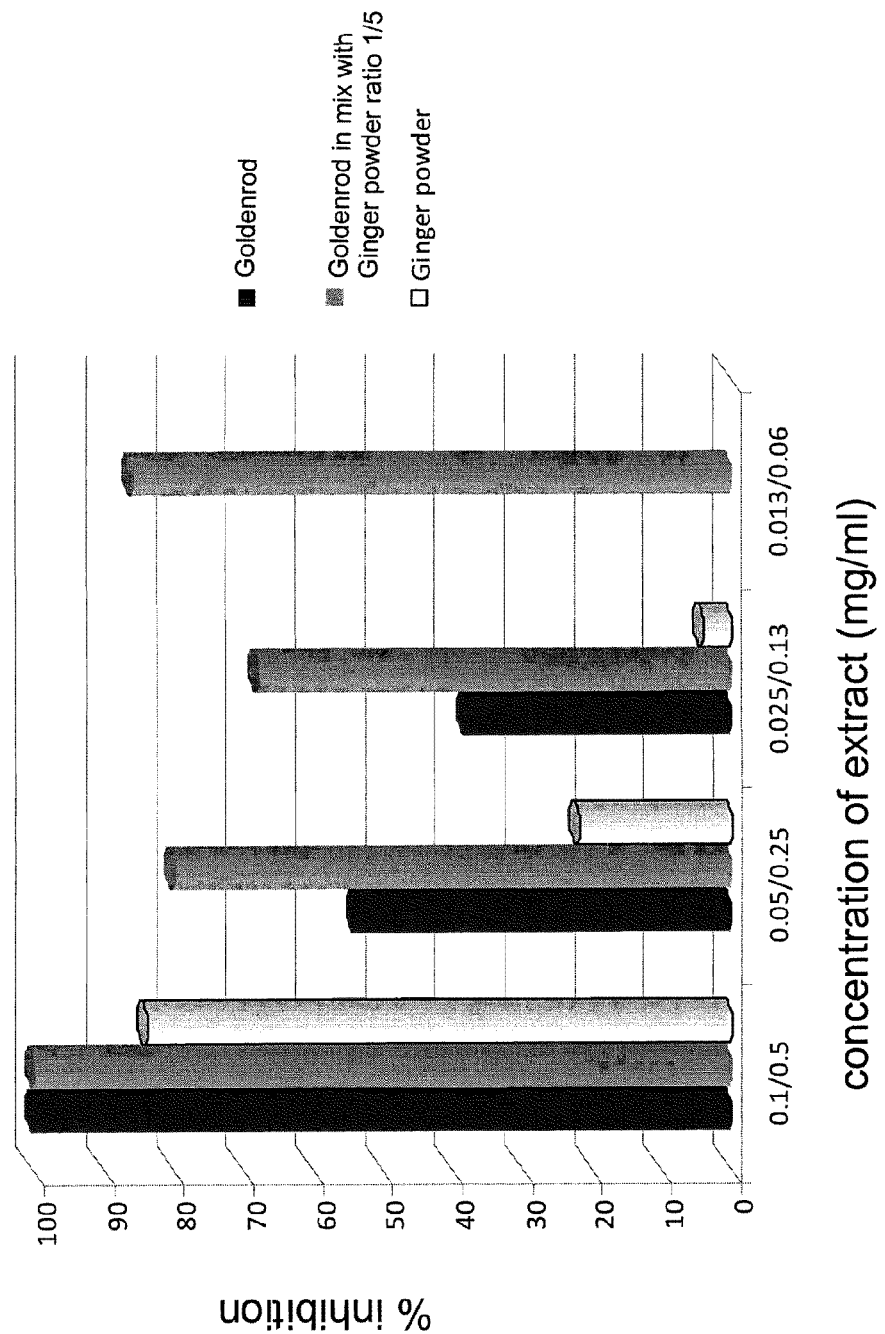
FIG. 2 shows the inhibitory (antiviral) effect of ginger powder, goldenrod extract (ETOH) and a combination thereof on Influenza virus capacity to infect (Plaque Forming Unit) an MDCK cell monolayer.

Similar results were obtained using ginger powder (dried and grinded whole ginger root) instead of ginger $CO_2$ extract (FIG. 2). The ratio of goldenrod:ginger powder was 1:5 for the experiments presented in FIG. 2. The results were compared with Tamiflu™ and Cold-Fx™ (data not shown). At a concentration of 1 mg/ml of Cold FX™ no inhibition was observed while 0.05 mg/ml of Tamiflu™ inhibited the formation of lysis plaques by 52%. Both products were therefore less efficient at reducing viral infection than the combination of goldenrod and ginger extracts of the present invention.

Example 2

In Vivo Antiviral Activity of Goldenrod Extract and Ginger Powder Against Influenza Virus Infection An animal model has allowed the Applicants to demonstrate that, when combined, the ginger powder and goldenrod extract also have the in vivo potential to interfere with the infection capability of influenza. In the animal model used, the ginger plant extract (whole ginger root powder) and the goldenrod dry hydroalcoholic extract (from Finzelberg, Germany) were combined in order to show a more significant activity.

Animal non-toxic doses of ginger powder, goldenrod extract and a combination thereof have been previously confirmed by the Applicants through in vivo toxicity assays (data not shown).

Ginger, goldenrod and a combination thereof were assayed in a recognized animal model related to the prevention and treatment of the influenza virus (Cottey R, 2001). In this study, the ginger was assayed as a dry plant (rhizome) of a $CO_2$ extract. However, the relative quantity of the ginger dry plant used was equivalent to the ginger $CO_2$ extract used in Example 1 (equivalent to the dry starting material). The ginger/goldenrod combination that was used also comprised blueberry dry powder. This formulation is named the Nutracan™ formulation and is described in Table II below.

TABLE II

Formulation of Nutracan ™

| | Relative Quantity (%) w/w |
|---|---|
| Medicinal ingredient | |
| Ginger powder (from Martin Bauer, Italy, product No. 3-992) | 41 |
| Goldenrod extract (from Finzelberg, product No. 0193305) | 8 |
| Blueberry powder (from Fruit d'or) | 20 |
| Non-medicinal ingredient | |
| Alcolec FF-100 powdered lecithin (from AMERICAN LECITHIN COMPANY) | 31 |

In this model, CD-1 mice (10 females per group) were inoculated intranasally with the influenza strain A/WS/33 (H1N1) at $1 \times 10^3$ PFU as determined in a preliminary study (data not shown). Groups were treated either 5 days prior to the infection (preventive arm) or the day of the infection (therapeutic/curative arm) with ginger powder (125 mg/kg), goldenrod extract (25 mg/kg) or a combination thereof (350 mg/kg of Nutracan™) Ginger powder, goldenrod extract and a combination thereof were compared to Tamiflu™ (Oseltamivir phosphate, from Roche, at 10 mg/kg, for therapeutic/curative arm) and to Cold-Fx® (CVT-E002, a ginseng-derived enriched fraction sold in Canada as a NHP for the prevention/attenuation of cold and flu symptoms, from CV Technologies, at 20 mg/kg, for the preventive arm). All these products were administered orally.

1) Seven groups of CD1 mice were randomized based on their weight (n=10). See Table III below for the description of each group, dosage regimen and duration of treatment for each, 2) Mice in the preventive arm groups were force-fed orally with a single daily dose of 100 μl of product for 5 days prior to infection, 3) On the day of infection (day 0), all mice were force-fed 4 hours prior to infection. All mice were then inoculated intranasally with the influenza virus strain A/WS/33, $10^3$ PFU contained in 30 μl of PBS. This was done under light anaesthesia of isofuran, 4) A single daily dose was given for all seven groups (4 preventive, 2 treatments and one control) till the end of the study, e.g., for 8 days, and 5) Apparent symptoms and weight were noted each day. Mice were sacrificed when their general state (including abnormal behaviour, determined by a veterinarian) had deteriorated or they had lost more than 20% of their weight.

TABLE III

Description of the mice groups assayed in the animal influenza infection model.

| Group | Product administrated | Daily dose | First day of dosage |
|---|---|---|---|
| 1 | Vehicle (PBS) | 100 μl | −5 |
| 2 | Tamiflu ® | 10 mg/kg | 0 |
| 3 | Cold-Fx ® | 20 mg/kg | −5 |
| 4 | Ginger powder + goldenrod extract (Nutracan ™ formulation) | 350 mg/kg | −5 |
| 5 | Ginger powder + goldenrod extract (Nutracan ™ formulation) | 350 mg/kg | 0 |
| 6 | Goldenrod extract | 25 mg/kg | −5 |
| 7 | Ginger powder | 125 mg/kg | −5 |

Figure 3:
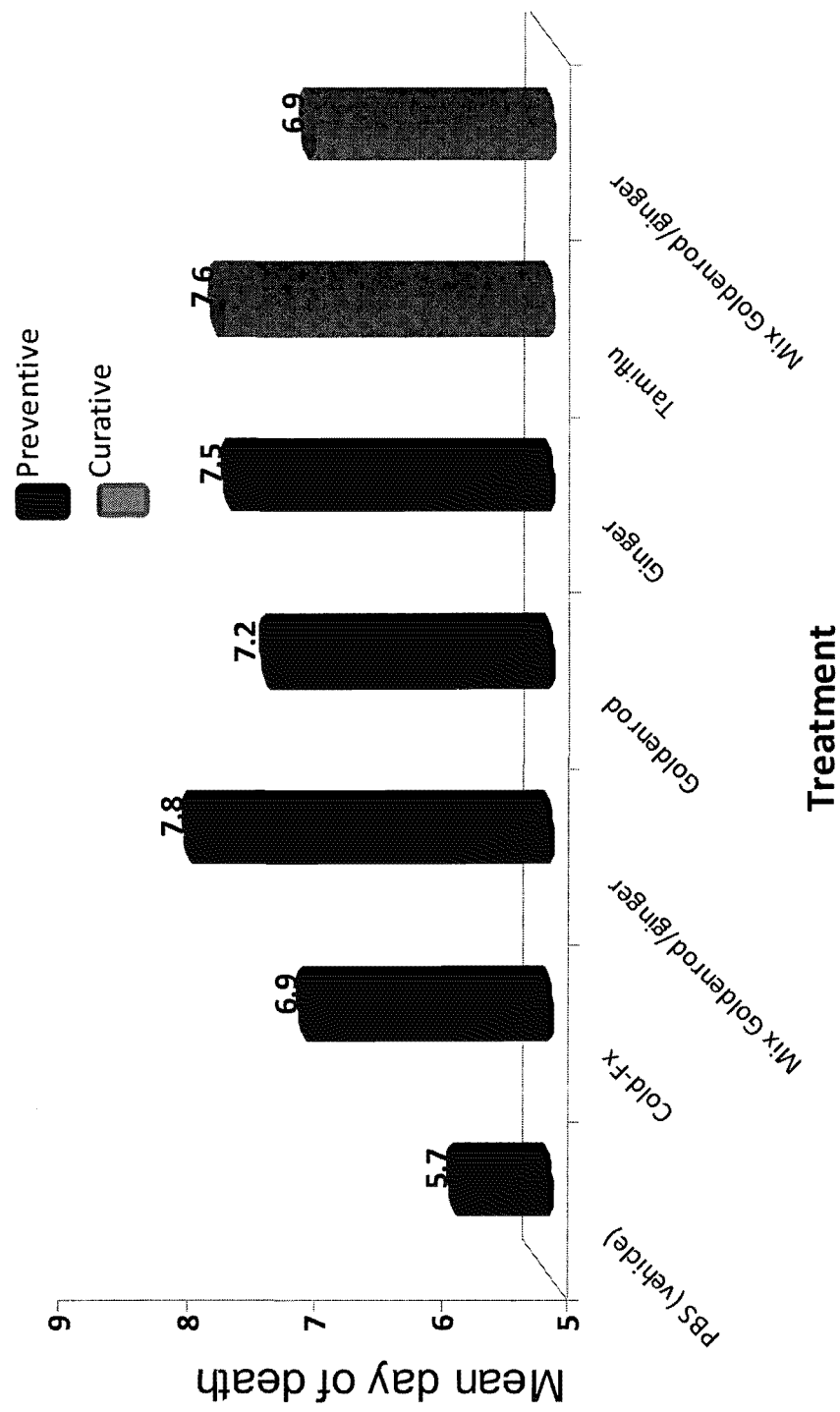
FIG. 3 shows the Mean Day of Death (MDD) of mice after infection with the influenza virus Strain A/WS/33. Preventive treatment (black) was given each day beginning 5 days prior to infection and Curative treatment (gray) was given beginning on the day of infection.

The data presented in FIG. 3 shows that the infected mice group (#4) treated preventively with the combination comprising ginger and goldenrod extracts presents a mean day of death (MDD) of 7.8 which is comparable to the effect of Tamiflu™'s curative treatment (MDD=7.6). All groups presented an increase in MDD when compared to the control group (MDD=5.7). In the preventive arm of the study, the combination of goldenrod and ginger (Nutracan™ formulation) was the group with the highest increase in MDD. Cold-Fx®, an NHP for the prevention and relief of cold and flu symptoms, was the lowest, although with a significant difference. In the curative arm, Tamiflu® was the most effective, but the difference between the vehicle group and the combination, (Nutracan™ formulation), was still statistically significant. It must be noted that there was a statistical difference between each group (preventive or curative) and the control group (p<0.002 or less). No mice of the control group survived after 6 days of the experiment, whereas the groups with treatment had different survival rates.

Table IV below summarizes the MDD value and provides statistical value for each group in the study. All groups had a significant value when compared to the control group without treatment.

TABLE IV p-value of MDD for all experimental groups compared to the control group.

| Group | Treatment (starting day) | MDD | p-value |
|---|---|---|---|
| 1 | Vehicle (−5) | 5.7 | |
| 2 | Tamiflu ™ 10 mg/kg (0) | 7.6 | <0.0001 |
| 3 | Cold-FX ™ 20 mg/kg (−5) | 6.9 | 0.0026 |
| 4 | Nutracan ™ 350 mg/kg (−5) | 7.8 | <0.0001 |
| 5 | Nutracan ™ 350 mg/kg (0) | 6.9 | 0.0026 |
| 6 | Solidago extract 25 mg/kg (−5) | 7.2 | <0.0001 |
| 7 | Ginger 125 mg/kg (−5) | 7.5 | <0.0001 |

Figure 4:
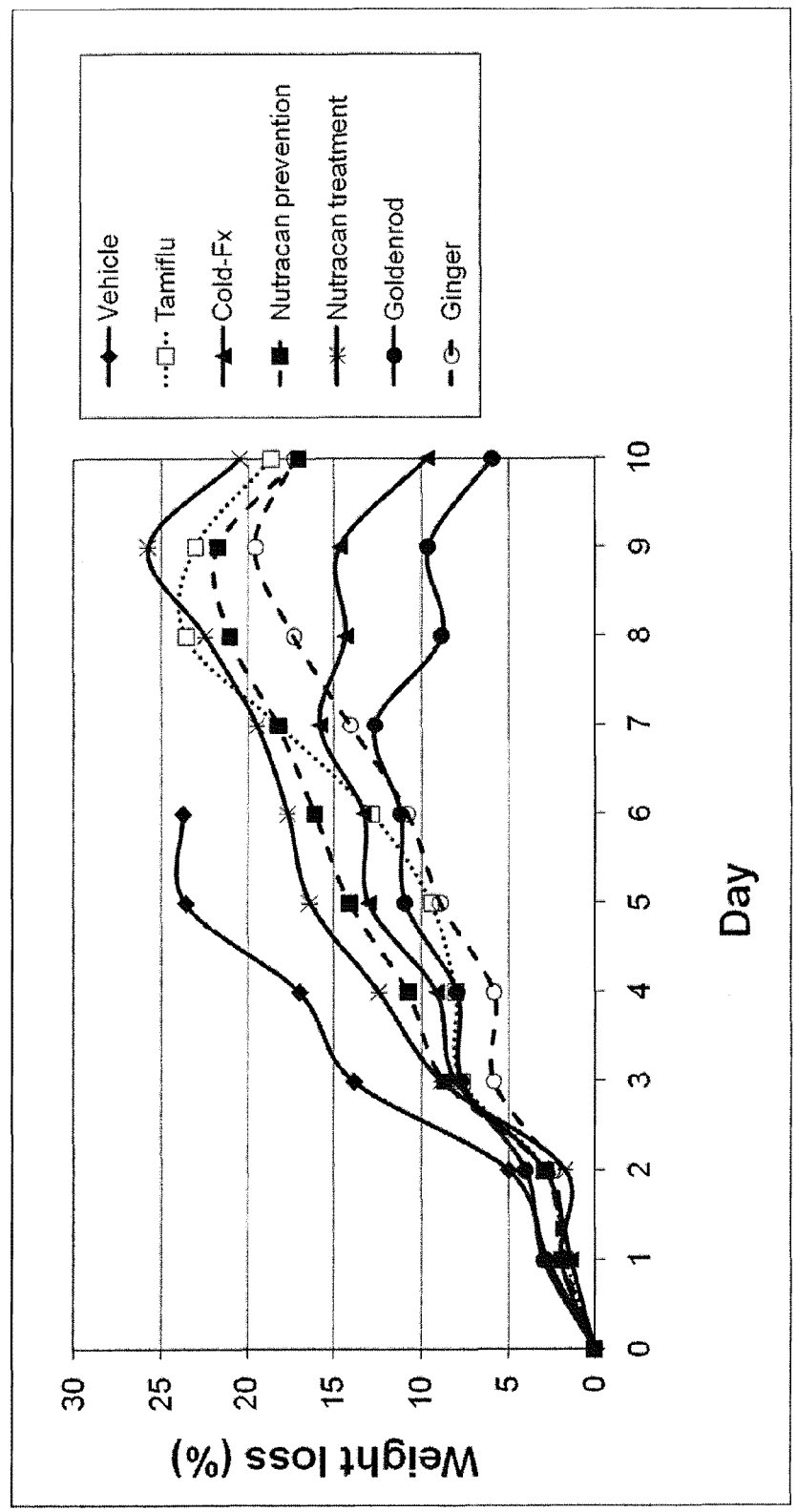
FIG. 4 shows the percentage of weight loss for each experimental group of mice after infection with the influenza virus Strain A/WS/33.

The effect of the extracts on the amount of weight loss following infection was also analyzed. The percentage of weight loss is represented in FIG. 4. The first 5 days prior to infection are not in the graph since there was no significant weight difference between groups. It is important to note that the difference is lower in the end since the mice remaining are those that survived the experiment.

Example 3

Antiviral Activity of Goldenrod and Ginger Extracts Against Cold Infections

Figure 5:
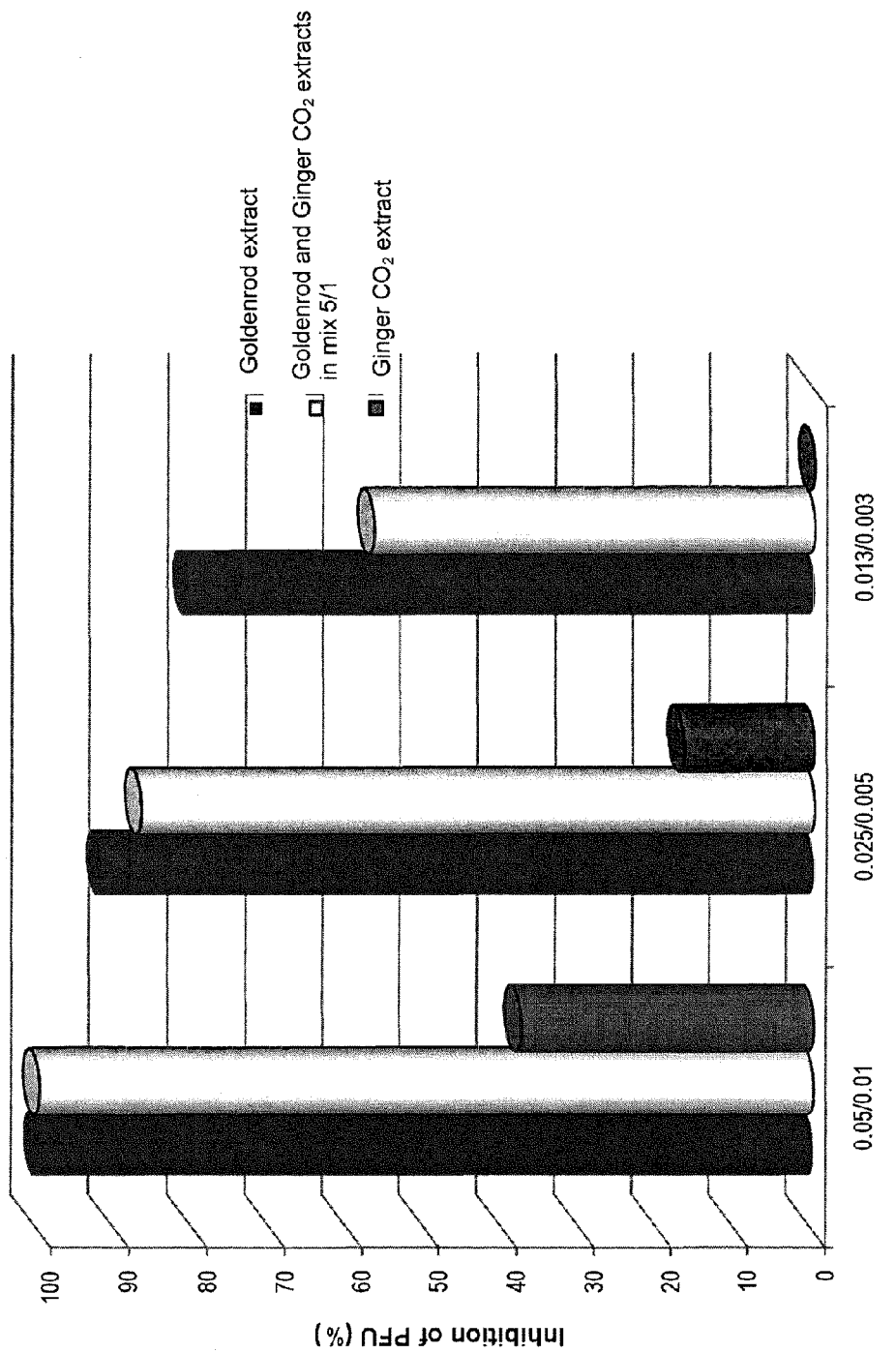
FIG. 5 shows the inhibitory (antiviral) effect of ginger $CO_2$ extract, goldenrod (*Solidago virgaurea*) extract (ETOH) and a combination thereof on rhinovirus virus capacity to infect (inhibition of Plaque Forming Unit) HELA cells in monolayer.

The antiviral activity of ginger ($CO_2$ extract, from Flavex, product no. 0.14.013) and goldenrod (*Solidago virgaurea*, Hydroalcoholic extract, Finzelberg product no. 0193305) was assessed against human cold infections. As shown in Table V below and FIG. 5, both goldenrod and ginger extracts (alone or in combination) inhibit rhinovirus infection, although goldenrod appears to be more efficient than ginger at the concentrations tested.

The antiviral activity was determined using a cellular model recognized as a standard way to analyze plaque formation by rhinovirus (Fiala M, 1968). This model uses a monolayer of HeLa cell line that is infected with a human rhinovirus, resulting in lysis plaques (infected cells area) that are then counted. In this analytical model, in presence of antiviral agents, the numbers of lysis plaques is decreased proportionally to the antiviral power of the tested agents.

Monolayers of HeLa cells (ATCC# CCL-2) were grown in 6-well culture plates until confluency. Before the infection or inoculation, the media was removed and cells were washed delicately once with pre-warmed DMEM supplemented with 30 mM of $MgCl_2$ and 2% fetal bovine serum. 200 μl of the tested product (goldenrod and/or ginger extract) were added at proper dilution in DMEM with 30 mM of $MgCl_2$ and 2% fetal bovine serum. Cells were then infected with the human rhinovirus 1A (ATCC #VR-1559), diluted in 200 μl of the same medium as the tested extracts. The plates were incubated for an hour at 33° C., 5% $CO_2$. After adsorption, the product and virus solution were removed and the cells were overlaid with 3 ml of a solution containing 1% agarose in pre-defined media containing the product. Vehicle was used as control. All assays were done in duplicate. Once overlaid, the plates were incubated at 33° C., 5% $CO_2$ in a humidified atmosphere for 2 days.

After the incubation, the plates were stained with Crystal Violet 0.1%. All wells were digitally photographed, plaques were counted and the inhibition of plaque formation for each dilution of product was calculated.

The inhibition is reported as percentage (%) of inhibition of infection as compared with infection in the absence of product. Percentage inhibition was calculated according to the formula:

$$\text{Percentage (\%) inhibition} = [C_A - C_B / C_A] \times 100$$

wherein $C_A$ is the number of plaque in the absence of a product or plant extract and $C_B$ is the count of plaque in the presence of the extract or their combination.

TABLE V

Antiviral activity of ginger and goldenrod extracts alone or in combination against human rhinovirus 1A (HRV-1A) infection

| ID | Concentration (mg/ml) | Inhibition of PFU (%) |
|---|---|---|
| PL208 50002 (goldenrod hydroalcoholic extract) | 0.05 | 100 |
| | 0.025 | 92 |
| | 0.0125 | 81 |
| PL202 50001 (ginger $CO_2$ extract) | 0.01 | 38 |
| | 0.005 | 17 |
| | 0.0025 | 0 |
| PL208 50002 + PL202 50001 | 0.05/0.01 | 100 |
| | 0.025/0.005 | 87 |
| | 0.0125/0.006 | 57 |

Example 4

Antiviral Activity of Goldenrod Alcoholic and Water Extracts

The antiviral activity of a water extract and of an alcoholic extract of various species of goldenrod against influenza virus A/WS/33 H1N1 was assessed as described in Example 1 on MDCK cell monolayer. The extraction with water was done as follows: 7.5 g of grinded goldenrod was extracted with agitation in 50 ml of water for 24 hours at room temperature, left with no agitation for another 24 hours and then centrifuged for 7 minutes at 1500 rpm. The supernatant was submitted to multiple filtrations, 40 µm, 1.2 µm, 0.45 µm and finally 0.2 µm.

Figure 6:
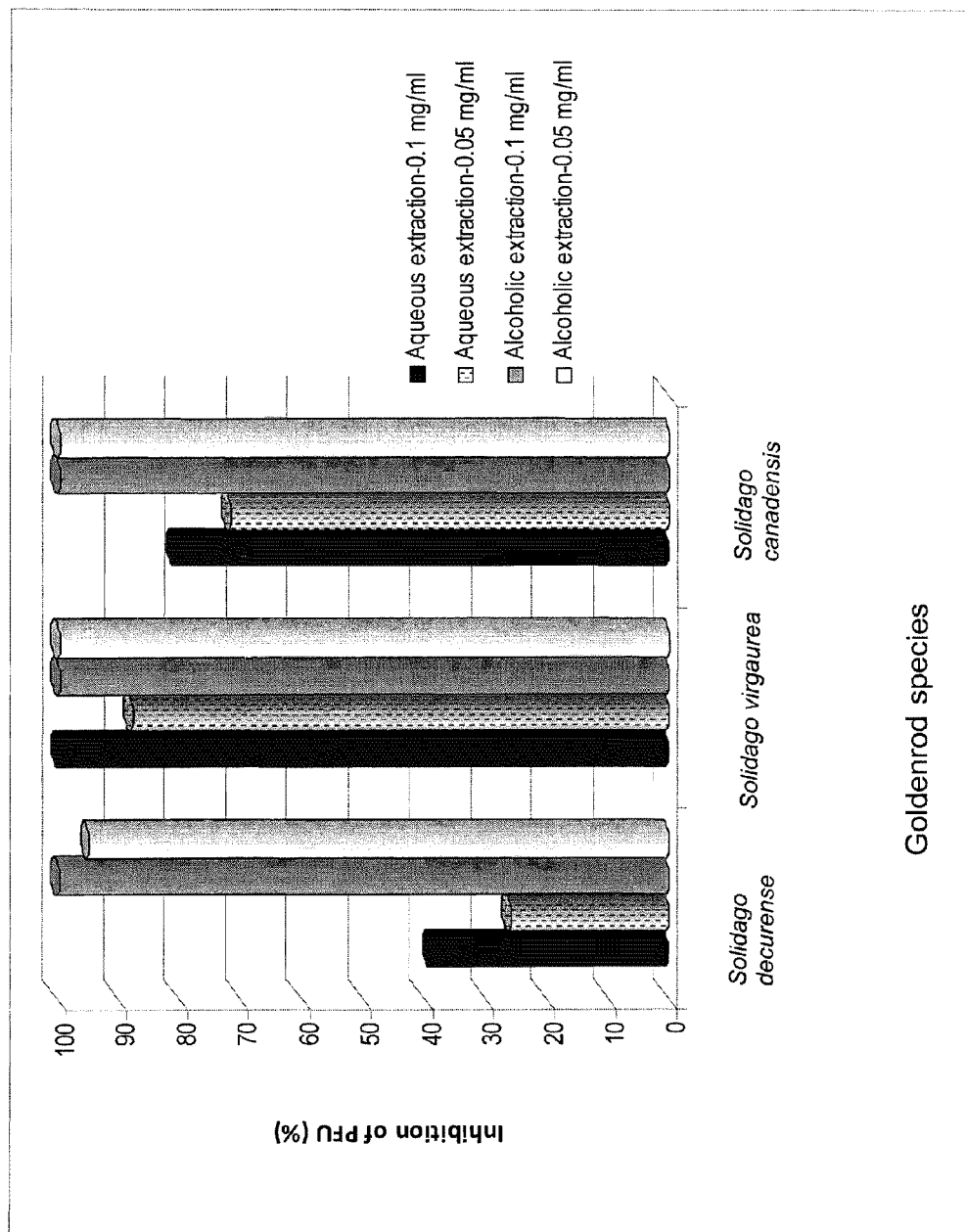
FIG. 6 shows the inhibitory (antiviral) effect of goldenrod extracts (ETOH and water) from various species (*Solidago decurense Lour*, *Solidago virgaurea* and *Solidago canadensis*) on influenza virus A/WS/33 N H1N1 capacity to infect (inhibition of PFU) MDCK cell monolayer.

Alcoholic extraction was as follows: 15 g of grinded goldenrod were macerated in 100 ml of methanol with a 10-minute reflux. The generated extract was submitted to multiple filtrations, 40 µm, 1.2 µm, and finally 0.2 µm The results presented in Table VI below and FIG. 6 show that for *Solidago decurense*, and *Solidago canadensis*, the alcoholic extract is much more efficient at inhibiting viral infection than the water extract. Similar results can be observed for *Solidago virgaurea*, although to a lesser extent. This difference is probably due to the concentrations tested (which are probably too high to clearly show a difference for this particular species). In addition, as observed for the aqueous extraction, among the species tested, *Solidago virgaurea* appears to be the most efficient at inhibiting viral infection, followed closely by *Solidago canadensis* and finally *Solidago decurense*.

TABLE VI

Antiviral activity of water and alcoholic extracts from various species of goldenrod

| Plant | Concentration (mg/ml) | Inhibition of PFU (%) Aqueous extraction | Inhibition of PFU (%) Alcoholic extraction |
|---|---|---|---|
| *Solidago decurense* | 0.1 | 39 | 100 |
| | 0.05 | 26 | 95 |
| *Solidago virgaurea* | 0.1 | 100 | 100 |
| | 0.05 | 88 | 100 |
| *Solidago canadensis* | 0.1 | 81 | 100 |
| | 0.05 | 72 | 100 |

Example 5

Antiviral Activity of Goldenrod and Ginger Extracts on the Human Pandemic H1N1/09 Influenza Virus (Swine Flu Virus)

The antiviral activity of goldenrod (*Solidago virgaurea*) and ginger extracts (alone and/or in combination) against Swine flu was tested and compared to that of Ribavarin and Oseltamivir.

The Antiviral and Toxicity Assays have been validated (Noah et Al., Antiviral Res. 2007 January; 73(1):50-9).

Materials and Methods

CellTiter-Glo® Detection Assay for Cell Viability

Measurement of influenza-induced CPE is based on quantitation of ATP, an indicator of metabolically active cells. The CPE assay employs a commercially available CellTiter-Glo® Luminescent Cell Viability Kit (Promega, Madison, Wis.), and is a reliable method for determining cytotoxicity and cell proliferation in culture. The procedure involves adding the single reagent (CellTiter-Glo® Reagent) directly to previously cultured, subconfluent cells in media. This induces cell lysis and the production of a bioluminescent signal (half-life greater than 5 hours, depending on the cell type) that is proportional to the amount of ATP present (which is a biomarker for viability).

Materials

Cells—Madin Darby canine kidney (MDCK), ATCC Cat # CCL-34; Human Influenza Virus A/CA/04/09 H1N1;—CellTiter-GLO—Promega; Substrate—Cat # G755B; Buffer—Cat # G756B; Control drugs—Ribavirin—MP Biomedicals, Inc., Cat #196066—Oseltamivir carboxylate (Southern research); and Test compounds: (ginger $CO_2$ extract and goldenrod hydroalcoholic extract). A minimum of one (1) milligram of each compound (2 mg in total) is required to perform the assay.

Methods

TABLE VII

Test Plate Layout and exemplary compound concentrations for dose response.

| | Experimental Ginger $CO_2$ extract (µg/ml) | | | | | Toxicity Ginger $CO_2$ extract (µg/ml) | | Experimental Goldenrod hydroalcoholic extract (µg/ml) | | | Toxicity Goldenrod hydroalcoholic extract (µg/ml) | | |
|---|---|---|---|---|---|---|---|---|---|---|---|---|---|
| Media | 30.00 | 30.00 | 30.00 | 30.00 | 30.00 | 150.00 | 150.00 | 150.00 | 150.00 | 150.00 | Virus |
| Control | 10.00 | 10.00 | 10.00 | 10.00 | 10.00 | 50.00 | 50.00 | 50.00 | 50.00 | 50.00 | Control |
| | 3.33 | 3.33 | 3.33 | 3.33 | 3.33 | 16.67 | 16.67 | 16.67 | 16.67 | 16.67 | |
| | 1.11 | 1.11 | 1.11 | 1.11 | 1.11 | 5.56 | 5.56 | 5.56 | 5.56 | 5.56 | |
| | 0.37 | 0.37 | 0.37 | 0.37 | 0.37 | 1.85 | 1.85 | 1.85 | 1.85 | 1.85 | |
| | 0.12 | 0.12 | 0.12 | 0.12 | 0.12 | 0.62 | 0.62 | 0.62 | 0.62 | 0.62 | |
| | 0.04 | 0.04 | 0.04 | 0.04 | 0.04 | 0.21 | 0.21 | 0.21 | 0.21 | 0.21 | |
| | 0.01 | 0.01 | 0.01 | 0.01 | 0.01 | 0.07 | 0.07 | 0.07 | 0.07 | 0.07 | |

Testing of H1N1/09

On day 1, MDCK cells were grown to 90% confluence, then trypsinized, recovered, centrifuged, and washed twice in PBS to remove residual serum. Afterward, the cells were diluted in BSA-containing DMEM, aliquoted into 96-well plates, and allowed to attach to the plate for 18 hours at 37° C.

On day 2, a visual observation confirmed cell viability. Test compounds (ginger $CO_2$ alcoholic goldenrod extract, and 5:1 goldenrod/ginger $CO_2$) were diluted to the appropriate test concentrations in BSA-containing media and were added to virus 2 hours before inoculation in 3 replicates. After the 2 hours, the compound with virus solutions were added to each CPE and the compounds with no virus was added to toxicity test wells. Plates were prepared as follows: 1) Untreated (media, negative control); 2) Treated with final concentrations of 0.01, 0.04, 0.12, 0.37, 1.1, 3.3, 10, 30 µg of ginger $CO_2$ (1:3 serial dilution, 3.3 log range, 8 doses); or 3) Treated with final concentrations of 0.07, 0.214, 0.62, 1.85, 5.56, 16.67, 50, 150 µg of goldenrod extract; or 4) Treated with final concentrations of 0.014/0.07, 0.04/0.214, 0.12/0.62, 0.37/1.85, 1.1/5.56, 3.3/16.67, 10/50, 30/150 µg of ginger $CO_2$/goldenrod extract 1/5; 5) Treated with final concentrations of 0.016, 0.033, 0.10, 0.33, 1.04, 3.3, 10.4, 33 µM of Oseltamivir; or 6) Treated with final concentrations of 0.046, 0.14, 0.4, 1.2, 3.7, 11.1, 33.3, 100 µM ribavirin in <1% DMSO. Final well volume was 100 µl (50 µl cells+25 µl drug 4× (or media)+25 µl virus 4× (or media)). The control virus was also incubated for 2 hours in media prior to inoculation.

Each conditions were added to the wells 1) virus (triplicates)—for antiviral efficacy (CPE) analysis; and 2) No virus (duplicates)—for toxicity analysis. Virus was added at 100 $TCID_{50}$ (100 times the tissue culture infectious dose that causes 50% lethality in 72 h, final concentration in the well is 1×)).

On Day 5 (72 h post virus addition), cell viability was measured by luminescence analysis using Promega CellTiter-Glo® kit.

Data Reporting

The raw data was then analyzed and compiled to provide: 1) Raw data and dose response curves for each treatment and virus strain; 2) Inhibitory concentration; 1050, 1090; 3) Raw data and toxicity profile for each treatment and virus strain; 4) Toxic concentration; TC50 and TC90; and 5) Therapeutic indices for each treatment and virus strain (see Table VIII below).

Figure 7:
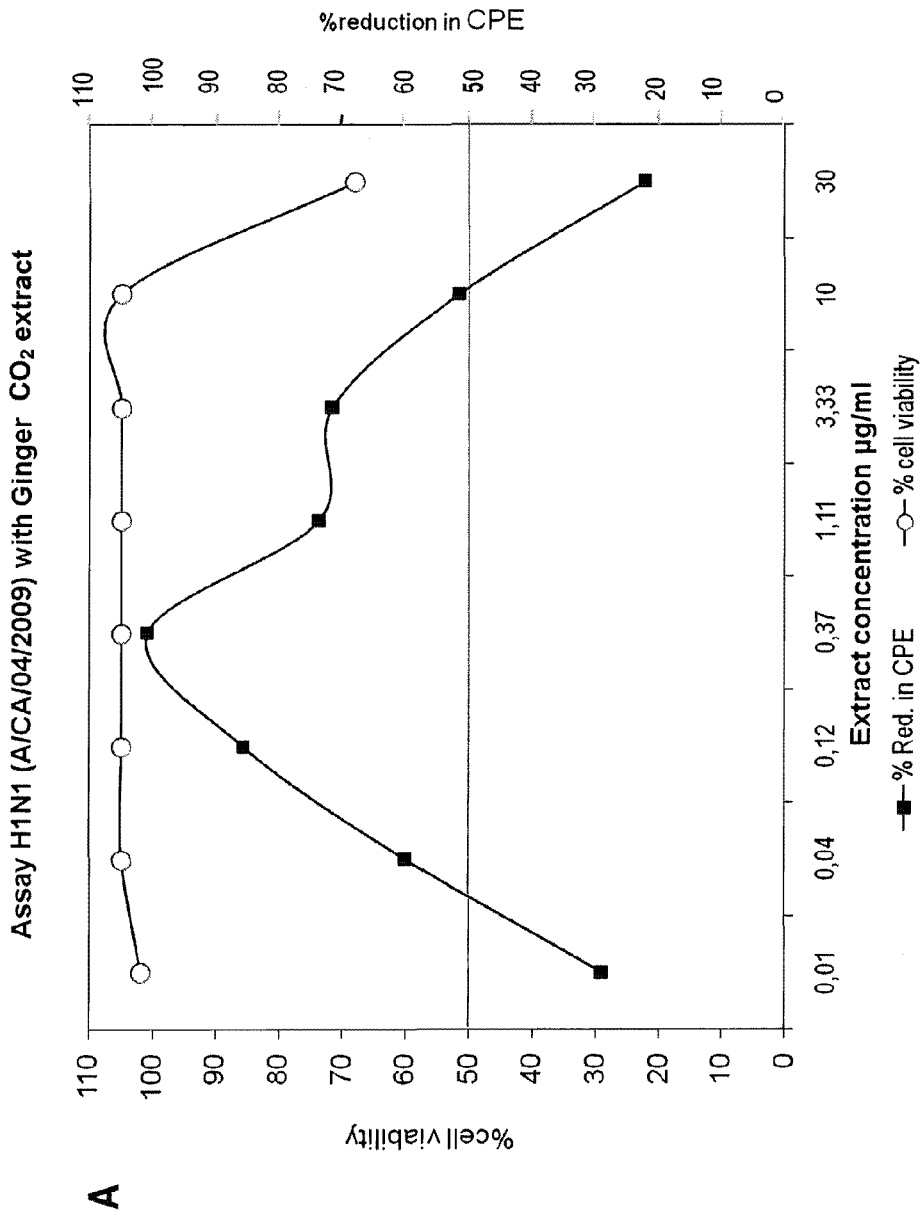
FIG. 7 shows the inhibitory (antiviral) effect of ginger $CO_2$ extract (A), goldenrod extract (ETOH) (B) and a combination ginger $CO_2$ extract/goldenrod extract (C) on Influenza A/CA/04/09 (H1N1) virus capacity to infect (PFU: Plaque Forming Unit) an MDCK cell monolayer.
Figure 7:
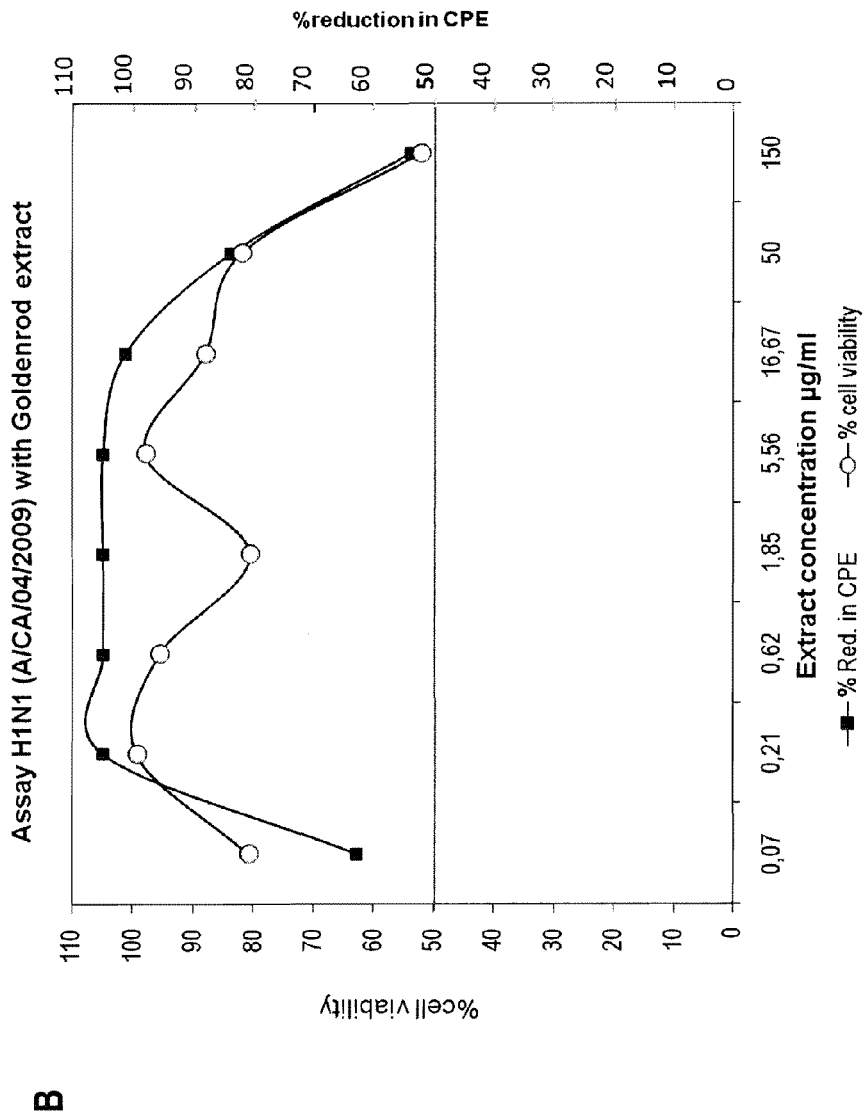
Figure 7:
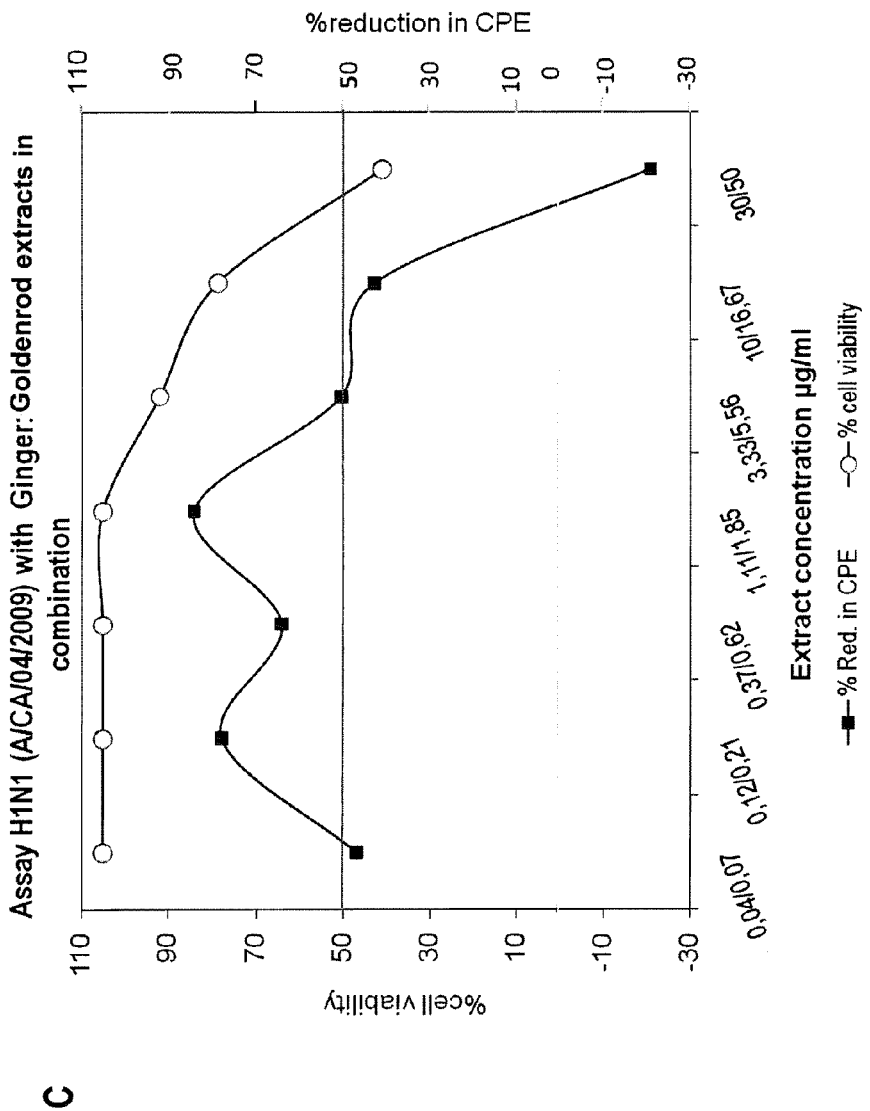

Following the above protocol, the goldenrod extract (PL208 50002) was shown to inhibit the Swine flu viral infection by 50% at a concentration lower than 0.07 µg/ml. The ginger $CO_2$ extract was shown to inhibit the same viral infection at a concentration of 0.02 µg/ml, and the mix (goldenrod/ginger $CO_2$) was shown to inhibit the viral infection by 50% at a concentration of 0.04:0.07 µg/ml. These results demonstrate a strong effect of goldenrod extract and ginger $CO_2$ extracts taken individually or mixed in a ratio of 5/1 (goldenrod:ginger, FIG. 7A-C). The results were compared with Tamiflu™ and Ribavarin™. Both products were less efficient at reducing Swine flu infection than the combination of goldenrod and ginger extracts and individual extracts of the present invention.

The highest cell viability observed when the compounds were tested individually is 99% at 0.21 µg/ml for PL208 and 101% at 0.37 µg/ml for PL202. The combination of the two compounds at these concentrations resulted in a cell viability of 120%, suggesting that the compounds have no cytotoxicity at these concentrations and are able to promote cell growth and prevent virus-induced cell death. It is clear from the data that this is the optimal concentration combination for the drugs. While synergy cannot be accurately determined because the cell viability values for the drugs used individually at these concentrations are at or above 100%, it does suggest some synergistic effect.

Example 6

Administration of Ginger and Goldenrod Extracts Within 48 Hours of the Onset on Symptoms Improves Treatment of Cold and Flu Infections Applicants have observed in anecdotic cases of human subjects who received ginger and goldenrod extracts, that administration of the Nutracan™ formulation (comprising ginger (powder) and *Solidago virgaurea* (Hydroalcoholic) extract—see Table 2 above) within 48 hours of the onset of cold and flu symptoms greatly increased the success of treatment. The composition of the present invention may thus advantageously be administered within 48 hours of the onset of the symptoms or as a preventive treatment (i.e., before the onset of the symptoms).

Example 7

Exemplary Oral Formulation Comprising a Goldenrod Hydroalcoholic Extract and a Ginger $CO_2$ Extract The following oral caplet formulation was prepared for the clinical assessment of the efficacy of the combination of the

TABLE VIII

Antiviral efficacy against Influenza H1N1 strain A/CA/04/09

| Compound | $IC_{50}$ (µg/ml) | $IC_{90}$ (µg/ml) | $TC_{50}$ (µg/ml) | $TC_{90}$ (µg/ml) | $SI_{50}$ (µg/ml) | $SI_{90}$ (µg/ml) |
|---|---|---|---|---|---|---|
| PL202 500001 (ginger $CO_2$ extract) | 1.029 | 0.17 | >30 | >30 | 1038 | 76 |
| PL208 500002 (goldenrod extract) | 0.0843 | 0.1753 | >150 | >150 | 1779 | 855 |
| BDI-630 (PL202:PL208) (goldenrod/ginger $CO_2$) | 0.04:0.07 | ND | 8:42 | 10:50 | 750 | ND |
| Tamiflu ™ (Oseltamivir) | 0.1 | ND | >10.3 | >10.3 | 0.1 | ND |
| Ribavirin | 5.26 | ND | >24.4 | >24.4 | 5.26 | ND | present invention. The formulation was a 450 mg capsule for oral administration. The product formulation is described in Table IX below and is designated BDI-630:

TABLE IX

Exemplary oral formulation prepared for clinical study

| Components | mg/capsule |
|---|---|
| Medicinal ingredients: | |
| Ginger $CO_2$ extract (from Flavex, product code 0.14.013) | 43.5 |
| Goldenrod hydroalcoholic extract (from Finzelberg, product no. 0193305) | 200.0 |
| Non-medicinal ingredients: | |
| Microcrystalline cellulose | 113.5 |
| Cross-linked sodium carboxymethyl cellulose | 6.0 |
| Stearic acid | 12.5 |
| Silica colloidal | 4.5 |
| Magnesium stearate | 3.5 |
| Calcium monohydrogen phosphate | 66.5 |
| Total: | 450.0 |

Example 8

In Vitro Antiviral Activity of a One-Shot Liquid Formulation of a Combination Comprising Ginger Powder and Goldenrod Extracts Against Influenza and Rhinovirus Virus Infections Applicants have demonstrated that ginger and goldenrod in a <<One-shot>> liquid formulation, show antiviral activity in cellular models described in Examples 1-3 above.

These experiments evaluate the organoleptic properties, pH, and taste (in fruit juice) of different combinations of ginger powder (rhizome/whole root) and goldenrod extract.

TABLE X

Identification of the different combinations and quantity of components for a liquid formulation

| Mix | Ginger powder (g) | Goldenrod extract (g) | 60 ml of liquid |
|---|---|---|---|
| B | 1 | 0.4 | $H_2O$ |
| C | 0.5 | 0.4 | $H_2O$ |
| G | 1 | 0.2 | $H_2O$ |
| H | 0.5 | 0.2 | $H_2O$ |

Concentration higher than 1 g in ginger were not suitable in taste and were not pursued.

Each of formulations B to H were tested for antiviral activity against influenza and rhinoviruse type 1A and type 2, and results were reported in Tables XI to XIII, respectively.

TABLE XI

Antiviral efficacy against Influenza strain A/WS/33 on MDCK cells

| Mix | IC50 (µg/ml) | TC50 (µg/ml) | SI50 TC50/IC50 |
|---|---|---|---|
| B | 14/5.6* | >250/100 | >19.2 |
| C | 3/2.4 | >125/100 | >41.6 |
| G | 78/15.6 | >250/50 | >3.2 |
| H | 21/8.4 | >125/50 | >6 |

TABLE XI-continued

Antiviral efficacy against Influenza strain A/WS/33 on MDCK cells

| Mix | IC50 (µg/ml) | TC50 (µg/ml) | SI50 TC50/IC50 |
|---|---|---|---|
| Ginger powder | ND | >250 | ND |
| Goldenrod extract | >0.78 | >100 | >128 |

*The results are presented in µg of ginger powder/µg goldenrod extract/ml

TABLE XII

Antiviral efficacy against Rhinovirus type 1A on Hela cells

| Mix | IC50 (µg/ml) | TC50 (µg/ml) | SI50 |
|---|---|---|---|
| B | 8/3.1 | 85/33.7 | 10.6 |
| C | 22/17.5 | >125/100 | >5.7 |
| G | 8/1.56 | >250/50 | >31.25 |
| H | 5/1.95 | >125/50 | >25 |
| Ginger powder | ND | ND | ND |
| Goldenrod extract | 90 | >100 | >1.1 |

TABLE XIII

Antiviral efficacy against Rhinovirus type 2 on Hela cells

| Mix | IC50 (µg/ml) | TC50 (µg/ml) | SI50 |
|---|---|---|---|
| B | >250/100 | >250/100 | ND |
| C | 58/46 | >125/100 | >2.2 |
| G | 8/1.56 | >250/50 | >31.25 |
| H | 46/18.4 | >125/50 | >2.7 |
| Ginger powder | ND | ND | ND |
| Goldenrod extract | 41 | >100 | >2.4 |

A liquid formulation (One-shot) is effective in vitro against influenza and rhinovirus infections. A synergy between ginger powder and goldenrod extract is observed in assay against Rhinovirus type 1A. In a specific embodiment, the formulation may be in a volume of approximately 60 ml of flavored juice. In a more specific embodiment, 60 ml of flavored juice contains a ratio of 0.5 g of ginger powder with 0.3 g of goldenrod extract.

Example 9

Clinical Study

The purpose of the clinical Study (No. BDI-URS-09-002): a double blind study using *Echinacea* capsules as the reference product) is to evaluate the safety and the preliminary clinical efficacy of the combination of the present invention (named BDI-630 in the clinical study protocol) in reducing the severity and duration of the symptoms associated with colds. The general approach to be followed during the double-blinded study is to compare the effect of a well-recognized NHP for the attenuation of cold symptoms, *Echinacea* (Echinamide™-*echinacae purpurea* extract plant:extract ratio of 2.4:1), to the combination of the present invention in Community-dwelling Adults (between 21 and 60 years old).

Following is a summary of the clinical protocol that will be used.

Trial Objectives

The objective of this pilot/exploratory clinical trial is to evaluate the effects of a specific formulation comprising a $CO_2$ supercritical extract obtained from ginger (*Zingiber officinale*) and a hydro-alcoholic extract obtained from goldenrod (*Solidago virgaurea* L.) as described in Example 7 (Table IX) versus Echinamide® (*Echinacea purpurea*) on the management (attenuation) of cold symptoms in community-dwelling adults (between 18 and 60 years old).

Study Design and Duration

Study BDI-URS-09-002 will be an exploratory, double-blinded, randomized, and controlled study, performed at centers in Québec, Canada during the winter season. Patients who have developed cold symptoms (within the last 36 hours) and have signed an Informed Consent Form (ICF) will be screened to assess their eligibility according to the inclusion & exclusion criteria.

Approximately 80 patients with clinically confirmed cold symptoms (defined below) as evaluated by a physician, will be randomized in order to obtain a minimum of 72 evaluable patients following the 10 day-treatment period (i.e., an approximate dropout rate of 10% is expected). Patients will be randomly allocated BDI-630 or Echinamide®. Randomized patients will start taking the Investigational Product on Day 1 (Screening and Randomization Visit) and will continue for a total of 10 days. Evaluation Visits will take place on Day 7 and Day 14. Patients will be monitored for safety assessments and for cold symptoms evaluations for up to 14 days. During the 14-day study, patients will be asked to complete the Wisconsin Upper Respiratory Symptom Survey—21 (WURSS-21) and a diary (to register daily adverse events, concomitant medications, daily doses of the Investigational Product). Patients will contact the Investigator if they experience Serious Adverse Events and an unscheduled (urgent) visit will be arranged for appropriate diagnosis and treatment, as determined by the Physician.

A clinically confirmed cold in this study is defined as follows: the patient reports at least 2 of the following symptoms (within the last 36 hours): runny nose, stuffy/plugged nose, sneezing, sore throat, scratchy throat, cough, hoarseness, head congestion, chest congestion and feeling tired/exhausted.

The duration of treatment with BDI-630 or Echinamide® for each patient is 10 days.

The total duration of the study for each patient is 14 Days. Patient visits are as follows: Day 1 (Screening and Randomization), Day 7 (Treatment Evaluation) and Day 14 (Post-Treatment Follow-up).

Sample Size

It is expected that at least 120 patients will be screened to randomize 80 eligible patients (40 patients on BDI-630 and 40 patients on Echinamide®) and that approximately 72 will complete this 14 day study, as an estimated 10% may dropout during the study.

Inclusion Criteria

Patients must fulfill all of the following criteria on Study Day 1 to be eligible for randomization into the study: 1. Have signed the Informed Consent Form (ICF); 2. Able to understand and comply with planned study procedures; 3. Aged between 18 and 60 years old; 4. Have clinically confirmed early symptoms of a cold as evaluated by the Investigator, using the WURSS-21 questionnaire; i.e., patient reports at least 2 of the following symptoms (during no more than the last 36 hours): runny nose, plugged nose, sneezing, sore throat, scratchy throat, cough, hoarseness, head congestion, chest congestion, feeling tired; 5. For a woman of child-bearing potential, a negative pregnancy test and agreement to avoid becoming pregnant (use of an effective method of contraception or abstinence) from the day of randomization and until 2 weeks after the end of treatment will be mandatory; 6. Able to attend all scheduled visits and comply with all trial procedures; and 7. Is generally in good health, as determined by medical history, vital signs (heart rate, blood pressure, oral temperature) and physical exam of the following body systems: ears, nose and throat; thorax, lungs; abdomen; cardiovascular; neurological; musculoskeletal; extremities; skin/dermatology; peripheral vascular; and any other examination deemed necessary by the Investigator.

Exclusion Criteria

Patients who meet any one of the following criteria on Study Day 1 are not eligible for randomization into the study: 1. Patients with suspected flu (influenza), streptococcus infection; asthma, pneumonia, avian influenza or swine influenza (H1N1), as determined by the Investigator or clinician; 2. Participation in investigating a vaccine, drug, medical device or a medical procedure in the 4 weeks preceding randomization (previous vaccination not involving a clinical trial is allowed); 3. Planned participation in any other clinical trial or study (not specified in the above paragraph) during the present study period; 4. Known or suspected impairment/alteration of immune function, for example, resulting from: (a) Use of long-term systemic corticosteroids (i.e., systemic Cortisone, Dexamethasone and/or other immunosuppressive medications, e.g., Imuran) within the last 3 months or nasal corticosteroid within the past 15 days or having the intent to receive such medication during the study; (b) History of Human Immunodeficiency Virus (HIV) infection, Hepatitis B or Hepatitis C, tuberculosis, rheumatoid arthritis, systemic lupus, collagen vascular diseases, multiple sclerosis; (c) History of congenital or acquired immunodeficiency, immunosuppressive therapy such as anti-cancer chemotherapy or radiation therapy within the preceding 6 months; (d) Receipt of parenteral immunoglobulin preparation, blood products and/or plasma derivates within the past 3 months or having the intent to receive such medication during the study; or (e) Use of other immunomodulators (i.e. Interleukins, Interferon); 5. Current or planned use of anticoagulants (e.g., warfarin, heparin, Aspirin®, Clopidogrel®), anti-inflammatory, antiviral, nasal decongestants containing corticosteroids or antihistamines, expectorants, lozenges, zinc, oral antihistamines, antibiotics, cough syrup, sleep medication (e.g., sleeping pills, caffeine pills) herbal supplements intended for the treatment of colds (including herbal tea), Cold Fx®, Airborn®, Echinilin®, ginseng, and vitamin C (multivitamins containing <100 mg vitamin C are allowed); 6. Known systemic hypersensitivity to ginger or goldenrod herb or *Echinacea*; 7. Known allergenic reaction to Asteraceae/Compositeae/family (e.g., ragweed, chrysanthemums, marigolds and daisies); 8. Known bleeding disorders; 9. Known renal diseases; 10. Known vesicular stones; 11. Patients suffering from unstable angina, or who had a myocardial infarction in the last 3 months, or who have a Grade II blood pressure (Systolic>160 mmHg and/or a diastolic>100 mmHg); 12. Current alcohol abuse or actively smoking marijuana or drug addiction (as it may interfere with the patient's ability to comply with trial procedures); 13. Surgery planned during the study or 30 days after the end of the study; or 14. Any condition, which, in the opinion of the Investigator, might interfere with the evaluation of the study objectives or would result in noncompliance with the protocol.

Drug Formulation

BDI-630 is a combination of two medicinal ingredients: Ginger (*Zingiber officinale*) root $CO_2$ extract and Goldenrod (*Solidago virgaurea*) aerial part hydroalcoholic extract. Each BDI-630 capsule contains 450 mg of the mixture+excipients (see Example 7 for detailed formulation).

Echinamide®: commercial product containing 250 mg of *Echinacea purpurea* per capsule. Capsules of Echinamide® will be inserted in identical white opaque capsules and packaged in the same plastic bottle used for BDI-630 to ensure blindness.

Dosage Regimen

From Day 1 to Day 7: A) BDI-630: 4 capsules/day (2 capsules, twice a day); 1,800 mg total daily dose; or B) Echinamide®: 4 capsules/day (2 capsules, twice a day); 1,000 mg total daily dose.

Supplies will be shipped to the Investigational site in equal proportions and the labels will have a number (associated with a blinded randomization code) but the site personnel will not know the code. The treatment products (BDI-630 or Echinamide®) will be supplied in bottles, each containing a 10-day supply. The bottles will be dispensed to the patient on Day 1 and the empty container will be returned on Day 14 to determine compliance and perform supply reconciliation.

After symptoms confirmation and randomization, BDI-630 or Echinamide® must be taken daily for 10 days. Evaluation visits will be as described in Table XIV below:

Concomitant Medication

Prohibited Medication/Therapies:
(1) Treatment with any other investigational drugs; or (2) the use of the following drugs throughout the entire study: immunomodulators (i.e., Interleukins, Interferon); systemic corticosteroids (i.e., systemic Cortisone, Dexamethasone and/or other immunosuppressive medications, i.e., Imuran); anticoagulants (e.g., warfarin, heparin, Aspirin®, Clopidogrel®); anti-inflammatory, antiviral, nasal decongestants containing corticosteroids or antihistamines; expectorants, lozenges, zinc, oral antihistamines, antibiotics, cough syrup; sleep medication (e.g., sleeping pills, caffeine pills); herbal supplements intended for the treatment of colds (including herbal tea), Cold Fx®, Airborn®, Echinilin®, ginseng; vitamin C (multivitamins containing <100 mg vitamin C are allowed).

Allowed Concomitant Medications:
Antipyretics (for patients with fever), i.e., acetaminophen (Tylenol®) and ibuprofen (Motrin® or Advil®); and nasal saline spray.

Premature Withdrawal/Discontinuation Criteria

At any time, a patient may be withdrawn from the study at his/her own request or on the basis of the Investigator's clinical judgment. However, patients who request to be withdrawn will be strongly encouraged to complete appropriate examinations for a valid evaluation of their case for its incorporation into the analysis. A patient who has not been randomized will be considered as "screening failure".

A patient who experiences an immediate hypersensitivity reaction (attributed to the treatment product) will be withdrawn from the study. Such reaction is defined as a systemic allergic reaction of immediate onset (within 1 hour post-dose) i) associated with hypotension or syncope; or ii) involving two or more organ systems.

TABLE XIV

Treatment/Assessment Visits

| Procedures | Day 1 Screening[1] | Day 1 Start of Treatment | Day 7 Treatment Evaluation | Day 14 Follow-up Evaluation | Unscheduled visit[2] |
|---|---|---|---|---|---|
| Randomization | | x | | | |
| Clinical laboratory (Haematology[3], Clinical Chemistry[3], Urinalysis[3], Coagulation test[3], blood serum[4]) | | x | x | x | x |
| Dispensing prevention dose (10-day-product supply)[7] | | x | | | |
| Patient diary completion[5] | | x | x | x | x |
| Concomitant medications (post-randomization) | | x | x | x | x |
| AEs or SAEs | | x | x | x | x |
| Physical examinations (post-randomization) | | | x | x | x |
| WURSS-21 Questionnaire for assessing severity of respiratory symptoms and QOL[6] | | x | x | x | |
| Return of bottles/blisters, assessment of compliance | | | | x | |

[1] Screening and Day 1 will be combined in one visit. The screen failures will be excluded before the Day 1 treatment and procedures;
[2] An unscheduled visit will only be performed for an urgent SAE evaluation, if it cannot be done at Day 7 or 14;
[3] The Clinical laboratory tests on Day-1 (to determine baseline) must be done post-randomization but before first treatment dose;
[4] Blood serum will be collected for future dosage of cytokines (Tumor Necrosis Factor and Interleukin-6) dosage. They will be kept frozen (at −70 degrees Celsius) until tests are performed;
[5] Patient will keep a diary as of Day 1 and will record data daily for 14 days. They will bring the diary at visits Day 7 and Day 14;
[6] The first WURSS-21 Questionnaire will be completed by the patients during the Day 1 visit, before the Physical exam and Investigator interview. The WURSS-21 Questionnaire must then be completed daily by the patients and could be completed prior to or during the Day 7 and Day 14 visits;
[7] The first dose should be administered at the Investigational site and patients should be kept under observation for 30 minutes (in case of an allergic reaction, to ensure appropriate treatment).

The Investigator should also provide in the Case Report Form (CRF) and source documentation a brief comment regarding the reason(s) and circumstances for withdrawal especially if a stop of treatment was not related to "lack of efficacy" or to "lack of tolerability".

A patient, who has been withdrawn with or due to an adverse effect and which has not been resolved at the time of withdrawal, should be followed up as clinically indicated.

Efficacy Variables and Analysis

The following efficacy endpoints will be evaluated: (a) The change in severity of common cold symptoms in total severity score (i.e., runny nose, plugged nose, sneezing, sore throat, scratchy throat, cough, hoarseness, head congestion, chest congestion, feeling tired) as compiled in the WURSS-21 questionnaires between Days 1 and 14; (b) The area under the curve (AUC) of the total severity score (i.e., runny nose, plugged nose, sneezing, sore throat, scratchy throat, cough, hoarseness, head congestion, chest congestion, feeling tired) based on the data compiled in the WURSS-21 questionnaires between Days 1 and 14; (c) The number of days with at least one WURSS-21 symptom with a score of 5 (moderate) or more (i.e., runny nose, plugged nose, sneezing, sore throat, scratchy throat, cough, hoarseness, head congestion, chest congestion, feeling tired) between Days 1 and 14; (d) Health-related quality of life measured by the quality of life (QOL) questions (i.e., think clearly; sleep well; breathe easily; walk, climb stairs, exercise; accomplish daily activities; work outside the home; work inside the home; interact with others; live your personal life) in the WURSS-21 Questionnaires compiled between Days 1 and 14; (e) Frequency, type and intensity of therapies and medication used against common cold from Days 1 to 14; and (f) the level of cytokines in blood serum.

Safety Variables and Analysis

Safety will be evaluated on the basis of treatment-emergent adverse events, laboratory measurements (clinical chemistry, cytokine levels, haematology, and urinalysis), and concomitant medications. The number and percentage of patients experiencing AEs and SAEs by type, frequency and intensity will be evaluated.

Statistical Analysis

The following populations will be analyzed in this study: (A) Safety population: Patients eligible for analysis will have received a minimum of one dose of the Investigational Product; and (B) Intent-to-treat population: Patients eligible for analysis are patients who have received a minimum of one dose of the Investigational Product and that were randomized, as classified by the arm to which the patient is randomized.

In order to evaluate hypotheses of variables in contingency tables, the Fisher exact test for proportions will be used. Multiple comparisons of time repeated data will be performed by repeated measures analysis of variance (ANOVA). In addition, descriptive statistics and graphical methods will be used to characterize the data.

REFERENCES

1. Altman, Lawrence K. (2006 Jan. 15). "This Season's Flu Virus Is Resistant to 2 Standard Drugs". *New York Times* (The New York Times Company)
2. Blumenthal M, Busse W R, Goldberg A, Gruenwald J, Hall T, Riggins C W and Rister R S. The complete German Commission E monographs. Therapeutic guide to herbal medicines. *American Botanical Council.* 1998, pp 135-140
3. Bridges C B, Thompson W W, Meltzer M I, et al. Effectiveness and cost-benefit of influenza vaccination of healthy working adults: a randomized controlled trial. JAMA 2000; 284: 1655-63
4. Gubareva L V (2004). "Molecular mechanisms of influenza virus resistance to neuraminidase inhibitors". *Virus Research* 103: 199-203
5. Hayden F G, Côté K M, Douglas Jr G R. Plaque inhibition assay for drug susceptibility testing on influenza viruses. *Antimicrobial Agents and Chemotherapy* 1980, 17(5):865-870
6. Hendrickson, R. Ed. *Remington: The Science and Practice of Pharmacy*, 21st ed.; Lippincott Williams & Wilkins: Baltimore Md., 2005.
7. Herrera G A, Iwane M K, Cortese M, Brown C, Gershman K, Shupe A, Averhoff F, Chaves S S, Gargiullo P, Bridges C B. Influenza vaccine effectiveness among 50-64-year-old persons during a season of poor antigenic match between vaccine and circulating influenza virus strains: Colorado, United States, 2003-2004. 2007 *Vaccine.* 2; 25(1):154-60
8. Klenk et al (2008). "Avian Influenza: Molecular Mechanisms of Pathogenesis and Host Range". *Animal Viruses: Molecular Biology*. Caister Academic Press. ISBN 978-1-904455-22-6
9. Nema, S. et al. Excipients and their use in injectable products, *PDA J. of Pharm. Science and Technol.*, 51(4), 166-171 (1997).
10. Roxas M, Jurenka N D, Jurenka J. Colds and Influenza: A review of diagnosis and conventional, botanical, and nutritional considerations. *Alternative Medicine Review* 2007, 12-1:25-48
11. Smith, Nicole M.; Joseph S. Bresee, David K. Shay, Timothy M. Uyeki, Nancy J. Cox, Raymond A. Strikas (2006 Jul. 28). "Prevention and Control of Influenza: Recommendations of the Advisory Committee on Immunization Practices (ACIP)". *Morbidity and Mortality Weekly Report*. Centers for Disease Control and Prevention. http://www.cdc.gov/mmwr/preview/mmwrhtml/rr5510a1.htm
12. Noah et. al, Antiviral Res. 2007 January; 73(1):50-9.
13. Cottey R, Rowe C A, Bender B S. Inflenza virus. *Current protocol in Immunology*. May 2001; Chapter 19: Unit 19.11.
14. Milan Fiala. Plaque Formation by 55 Rhinovirus Serotypes. *Appl Environ Microbiol.* 1968; 16(10): 1445-1450

The invention claimed is:

1. A method of preventing and/or treating a flu infection in a subject in need thereof comprising administering to the subject an effective amount of a composition comprising a combination of ginger and goldenrod, wherein the ginger: goldenrod ratio is about 1:5 or about 5:1, and whereby the flu infection is prevented or treated.

2. The method of claim 1, wherein the composition further comprises at least one non-medicinal ingredient.

3. The method of claim 1, wherein the composition comprises ginger in the form of a ginger extract and/or goldenrod in the form of a goldenrod extract.

4. The method of claim 1, wherein the composition comprises ginger in the form of ginger powder.

5. The method of claim 3, wherein the ginger extract is a crude ginger extract.

6. The method of claim 5, wherein the ginger extract is a crude 100% water ginger extract.

7. The method of claim 3, wherein the ginger extract is a $CO_2$ ginger extract.

8. The method of claim 3, wherein the goldenrod extract is a crude goldenrod extract.

9. The method of claim 8, wherein the goldenrod extract is a crude 100% water goldenrod extract.

10. The method of claim 3, wherein the goldenrod extract is an alcoholic goldenrod extract.

11. The method of claim 10, wherein the alcoholic goldenrod extract is a hydroalcoholic goldenrod extract.

12. The method of claim 11, wherein the alcohol used for production of the hydroalcoholic extract comprises a primary alcohol.

13. The method of claim 12, wherein the primary alcohol comprises methanol, ethanol, 1-propanol, 1-butanol or any combination thereof.

14. The method of claim 13, wherein the primary alcohol is ethanol.

15. The method of claim 14, wherein the alcohol used for production of the hydroalcoholic extract comprises a secondary alcohol.

16. The method of claim 10, wherein a mixture of at least two different alcohols is used for production of the alcoholic extract.

17. The method of claim 10, wherein the alcoholic extract is prepared using a solution comprising between about 20% and between about 85% of alcohol.

18. The method of claim 17, wherein the alcoholic extract is prepared using a solution comprising about 60% of alcohol.

19. The method of claim 17, wherein the alcoholic extract is prepared using a solution comprising about 30% of alcohol.

20. The method of claim 1, wherein the ratio is about 1:5 of ginger:goldenrod.

21. The method of claim 1, wherein the ratio is about 6:1 of ginger:goldenrod.

22. The method of claim 1, wherein the effective amount comprises between about 40 mg and about 4500 mg of ginger.

23. The method of claim 22, wherein the effective amount comprises between about 40 mg and about 200 mg of ginger.

24. The method of claim 23, wherein the effective amount comprises between about 43.5 mg and about 174 mg of ginger.

25. The method of claim 22, wherein the effective amount comprises between about 1000 mg and about 4500 mg of ginger.

26. The method of claim 22, wherein the effective amount comprises between about 2000 mg and about 4000 mg of ginger.

27. The method of claim 1, wherein the effective amount comprises between about 200 mg and about 800 mg of goldenrod.

28. The method of claim 27, wherein the effective amount comprises between 400 mg and about 800 mg of goldenrod extract.

29. The method of claim 1, wherein the composition further comprises a blueberry powder.

30. The method of claim 1, wherein the ginger is *Zingiber officinale Roscoe*.

31. The method of claim 1, wherein the goldenrod is *Solidago virgaurea*.

32. The method of claim 1, wherein ginger and goldenrod are the sole medicinal ingredients for the treatment of flu infections in the composition.

33. The method of claim 2, wherein the at least one non-medicinal ingredient is microcrystalline cellulose, cross-linked sodium carboxymethyl cellulose, stearic acid, silica colloidal, magnesium stearate and/or calcium monohydrogen phosphate.

34. The method of claim 1, wherein the composition is a nutraceutical or dietary or veterinary composition.

35. The method of claim 1, wherein the composition is a food supplement.

36. The method of claim 1, wherein the composition is comprised in a beverage or food product.

37. The method of claim 36, wherein the beverage is a 2 to 6 oz shooter beverage.

38. The method of claim 1, wherein the composition is administered within 48 h of the onset of flu symptoms.

39. The method of claim 1, wherein the composition is administered within 24 h of the onset of flu symptoms.

40. The method of claim 1, wherein the composition is administered twice daily.

41. The method of claim 1, wherein the composition prevents and/or treats at least one of the following symptoms: the viral titer in the subject's blood or cells, runny nose, plugged nose, sneezing, sore throat, scratchy throat, cough, hoarseness, head congestion, chest congestion, exhaustion, fever, muscle pain, loss of appetite, headache and chills.

42. The method of claim 41, wherein the composition prevents and/or treats at least two of the symptoms.

43. The method of claim 1, wherein the subject is a non-human animal.

44. The method of claim 5, wherein the ginger extract is an alcoholic ginger extract.

* * * * *